(12) United States Patent
Melker et al.

(10) Patent No.: US 8,211,035 B2
(45) Date of Patent: Jul. 3, 2012

(54) SYSTEM AND METHOD FOR MONITORING HEALTH USING EXHALED BREATH

(75) Inventors: Richard J. Melker, Gainesville, FL (US); David G. Bjoraker, Gainesville, FL (US); Samsun Lampotang, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 1521 days.

(21) Appl. No.: 11/512,856

(22) Filed: Aug. 29, 2006

(65) Prior Publication Data

US 2007/0203448 A1  Aug. 30, 2007

Related U.S. Application Data

(63) Continuation of application No. 11/301,911, filed on Dec. 13, 2005, which is a continuation-in-part of application No. PCT/US2005/006355, filed on Feb. 28, 2005, which is a continuation-in-part of application No. 10/788,501, filed on Feb. 26, 2004, now abandoned, which is a continuation-in-part of application No. 10/178,877, filed on Jun. 24, 2002, now Pat. No. 6,981,947, which is a continuation-in-part of application No. 10/054,619, filed on Jan. 22, 2002, now Pat. No. 7,104,963.

(51) Int. Cl.
*A61B 5/08* (2006.01)
*A61M 31/00* (2006.01)

(52) U.S. Cl. ........................ 600/532; 604/512

(58) Field of Classification Search .......... 600/529–543, 600/484, 483, 481; 128/203.12, 203.14, 128/204.23, 204.18; 604/512
See application file for complete search history.

(56) References Cited

U.S. PATENT DOCUMENTS

| 3,567,029 A | 3/1971 | Quame |
| 3,608,546 A | 9/1971 | Shinn |
| 3,649,199 A | 3/1972 | Littlejohn |
| 3,792,272 A | 2/1974 | Harte et al. |
| 3,877,291 A | 4/1975 | Hoppesch et al. |
| 3,951,607 A | 4/1976 | Fraser |

(Continued)

FOREIGN PATENT DOCUMENTS

DE    19 607 646 A1    9/1997

(Continued)

OTHER PUBLICATIONS

Hammon III, W. S. et al., "Forensic GPR: Finite-Difference Simulations of Responses From Buried Human Remains," *Journal of Applied Geophysics*, 2000, vol. 45, pp. 171-186.

(Continued)

*Primary Examiner* — Navin Natnithithadha
(74) *Attorney, Agent, or Firm* — Thomas, Kayden, Horstemeyer & Risley, LLP

(57) ABSTRACT

The present invention includes systems and methods for monitoring endogenous compound concentration in blood by detecting markers, such as odors, upon exhalation by a patient, wherein such markers are the endogenous compound itself or result from the endogenous compound. In the case of olfactory markers, the invention preferably utilizes electronic sensor technology, such as the commercial devices referred to as "artificial" or "electronic" noses or tongues, to non-invasively monitor endogenous compound levels in blood. The invention further includes a reporting system capable of tracking endogenous compound concentrations in blood (remote or proximate locations) and providing the necessary alerts with regard to emergent or harmful conditions in a patient.

27 Claims, 9 Drawing Sheets

U.S. PATENT DOCUMENTS

| | | |
|---|---|---|
| 3,955,926 A | 5/1976 | Fischer |
| 4,150,670 A | 4/1979 | Jewett et al. |
| 4,202,352 A | 5/1980 | Osborn |
| 4,215,409 A | 7/1980 | Strowe |
| 4,312,228 A | 1/1982 | Wohltjen |
| 4,314,564 A | 2/1982 | Albarda |
| 4,334,540 A | 6/1982 | Preti et al. |
| 4,346,584 A | 8/1982 | Boehringer |
| 4,349,626 A | 9/1982 | Labows et al. |
| 4,361,026 A | 11/1982 | Muller et al. |
| 4,399,686 A | 8/1983 | Kindlund et al. |
| 4,432,226 A | 2/1984 | Dempster |
| 4,456,014 A | 6/1984 | Buck et al. |
| 4,534,360 A | 8/1985 | Williams |
| 4,734,777 A | 3/1988 | Okino et al. |
| 4,735,777 A | 4/1988 | Mitsui et al. |
| 4,772,559 A | 9/1988 | Preti et al. |
| 4,796,639 A | 1/1989 | Snow et al. |
| 4,868,545 A | 9/1989 | Jones |
| 4,895,017 A | 1/1990 | Pyke et al. |
| 4,938,928 A | 7/1990 | Koda et al. |
| 4,992,244 A | 2/1991 | Grate |
| 5,003,985 A | 4/1991 | White et al. |
| 5,034,192 A | 7/1991 | Wrighton et al. |
| 5,042,501 A | 8/1991 | Kenny et al. |
| 5,046,018 A * | 9/1991 | Flewelling et al. ............. 702/24 |
| 5,060,506 A | 10/1991 | Douglas |
| 5,071,770 A | 12/1991 | Kolesar, Jr. |
| 5,081,871 A | 1/1992 | Glaser |
| 5,082,630 A | 1/1992 | Partin et al. |
| 5,094,235 A | 3/1992 | Westenskow et al. |
| 5,111,827 A | 5/1992 | Rantala |
| 5,137,692 A | 8/1992 | Fritz |
| 5,145,645 A | 9/1992 | Zakin et al. |
| 5,167,972 A | 12/1992 | Greenberg et al. |
| 5,179,027 A | 1/1993 | Fisher |
| 5,231,591 A * | 7/1993 | Flewelling et al. ............. 702/24 |
| 5,252,292 A | 10/1993 | Hirata et al. |
| 5,296,706 A | 3/1994 | Braig et al. |
| 5,303,575 A | 4/1994 | Brown et al. |
| 5,317,156 A | 5/1994 | Cooper et al. |
| 5,325,704 A | 7/1994 | Mariani et al. |
| 5,351,522 A | 10/1994 | Lura |
| 5,352,195 A * | 10/1994 | McEwen .................... 604/66 |
| 5,361,771 A | 11/1994 | Craine et al. |
| 5,409,839 A | 4/1995 | Balestrieri et al. |
| 5,425,374 A | 6/1995 | Ueda et al. |
| 5,447,165 A | 9/1995 | Gustafsson |
| 5,453,359 A | 9/1995 | Gargan et al. |
| 5,465,608 A | 11/1995 | Lokshin et al. |
| 5,466,700 A | 11/1995 | Batenhorst et al. |
| 5,482,601 A | 1/1996 | Ohshima et al. |
| 5,495,744 A | 3/1996 | Ueda et al. |
| 5,501,212 A | 3/1996 | Psaros |
| 5,528,924 A | 6/1996 | Wajid et al. |
| 5,547,878 A | 8/1996 | Kell |
| 5,558,083 A | 9/1996 | Bathe et al. |
| 5,560,352 A | 10/1996 | Heim et al. |
| 5,571,401 A | 11/1996 | Lewis et al. |
| 5,573,005 A | 11/1996 | Ueda et al. |
| 5,573,955 A | 11/1996 | Khanna et al. |
| 5,605,612 A | 2/1997 | Park et al. |
| 5,634,517 A | 6/1997 | Linden et al. |
| 5,645,072 A | 7/1997 | Thrall et al. |
| 5,716,852 A | 2/1998 | Yager et al. |
| 5,756,879 A | 5/1998 | Yamagishi et al. |
| 5,771,890 A | 6/1998 | Tamada |
| 5,776,783 A | 7/1998 | Kell |
| 5,783,154 A | 7/1998 | Althainz et al. |
| 5,783,449 A | 7/1998 | Kuznetsov |
| 5,795,787 A | 8/1998 | Silkoff et al. |
| 5,801,297 A | 9/1998 | Mifsud et al. |
| 5,826,577 A | 10/1998 | Perroz et al. |
| 5,830,412 A | 11/1998 | Kimura et al. |
| 5,861,254 A | 1/1999 | Schneider et al. |
| 5,866,434 A | 2/1999 | Massey et al. |
| 5,891,398 A | 4/1999 | Lewis et al. |
| 5,900,552 A | 5/1999 | Chu et al. |
| 5,918,257 A | 6/1999 | Mifsud et al. |
| 5,925,014 A | 7/1999 | Teeple Jr. |
| 5,928,167 A | 7/1999 | Wagner et al. |
| 5,932,877 A | 8/1999 | Braig et al. |
| 5,945,069 A | 8/1999 | Buehler |
| 5,950,630 A | 9/1999 | Portwood et al. |
| 5,954,685 A | 9/1999 | Tierney |
| 5,958,896 A | 9/1999 | Renshaw et al. |
| 5,962,335 A | 10/1999 | Katzman |
| 5,971,937 A | 10/1999 | Ekström |
| 5,996,586 A | 12/1999 | Phillips |
| 6,007,775 A | 12/1999 | Yager |
| 6,010,459 A | 1/2000 | Silkoff et al. |
| 6,025,200 A | 2/2000 | Kaish et al. |
| 6,057,162 A | 5/2000 | Rounbehler et al. |
| 6,063,243 A | 5/2000 | Zettl et al. |
| 6,067,167 A | 5/2000 | Atkinson et al. |
| 6,074,345 A | 6/2000 | van Oostrom et al. |
| 6,085,576 A | 7/2000 | Sunshine et al. |
| 6,094,681 A | 7/2000 | Shaffer et al. |
| 6,097,485 A | 8/2000 | Lievan |
| 6,120,443 A | 9/2000 | Cohen-Laroque |
| 6,131,571 A | 10/2000 | Lampotang et al. |
| 6,136,801 A | 10/2000 | Kell |
| 6,153,147 A | 11/2000 | Craig |
| 6,180,414 B1 | 1/2001 | Katzman |
| 6,186,977 B1 | 2/2001 | Andrews et al. |
| 6,190,858 B1 | 2/2001 | Persaud et al. |
| 6,203,814 B1 | 3/2001 | Fisher et al. |
| 6,216,690 B1 | 4/2001 | Keitel et al. |
| 6,221,026 B1 | 4/2001 | Phillips |
| 6,234,006 B1 | 5/2001 | Sunshine et al. |
| 6,237,397 B1 | 5/2001 | Shinar et al. |
| 6,244,096 B1 | 6/2001 | Lewis et al. |
| 6,248,078 B1 | 6/2001 | Risby et al. |
| 6,251,082 B1 | 6/2001 | Rayburn |
| 6,261,783 B1 | 7/2001 | Jayasena et al. |
| 6,264,913 B1 | 7/2001 | Wagner |
| 6,277,081 B1 | 8/2001 | Susi et al. |
| 6,283,953 B1 | 9/2001 | Ayer et al. |
| 6,303,316 B1 | 10/2001 | Kiel et al. |
| 6,305,212 B1 | 10/2001 | Drzewiecki |
| 6,312,390 B1 | 11/2001 | Phillips |
| 6,319,724 B1 | 11/2001 | Lewis et al. |
| 6,328,708 B1 | 12/2001 | Georgieff |
| 6,341,520 B1 | 1/2002 | Satoh et al. |
| 6,363,772 B1 | 4/2002 | Berry |
| 6,387,329 B1 | 5/2002 | Lewis et al. |
| 6,399,302 B1 | 6/2002 | Lannigan et al. |
| 6,416,479 B1 | 7/2002 | Seidman |
| 6,455,319 B1 | 9/2002 | Lewis et al. |
| 6,467,333 B2 | 10/2002 | Lewis et al. |
| 6,479,019 B1 | 11/2002 | Goldstein et al. |
| 6,495,824 B1 | 12/2002 | Atkinson |
| 6,511,453 B2 | 1/2003 | Georgieff |
| 6,558,626 B1 | 5/2003 | Aker et al. |
| 6,589,727 B1 | 7/2003 | Klenerman et al. |
| 6,597,438 B1 | 7/2003 | Cabuz et al. |
| 6,598,459 B1 | 7/2003 | Fu |
| 6,599,253 B1 | 7/2003 | Baum et al. |
| 6,599,281 B1 | 7/2003 | Struys et al. |
| 6,620,800 B1 | 9/2003 | Roberts, II |
| 6,631,333 B1 | 10/2003 | Lewis et al. |
| 6,680,377 B1 | 1/2004 | Stanton et al. |
| 6,727,075 B2 | 4/2004 | Fitzgerald et al. |
| 6,745,764 B2 * | 6/2004 | Hickle ................ 128/203.12 |
| 6,755,783 B2 | 6/2004 | Cosentino et al. |
| 6,807,965 B1 * | 10/2004 | Hickle ................ 128/204.23 |
| RE38,728 E | 4/2005 | Katzman et al. |
| 6,981,947 B2 * | 1/2006 | Melker .................... 600/532 |
| 6,986,347 B2 * | 1/2006 | Hickle ................ 128/200.24 |
| 7,034,692 B2 * | 4/2006 | Hickle ................... 340/573.1 |
| 7,104,963 B2 * | 9/2006 | Melker et al. .............. 600/532 |
| 7,152,604 B2 | 12/2006 | Hickle et al. |
| 7,364,552 B2 * | 4/2008 | Kiesele et al. ............. 600/532 |
| 2001/0021815 A1 | 9/2001 | Katzman et al. |
| 2001/0041366 A1 | 11/2001 | Lewis et al. |
| 2001/0046674 A1 | 11/2001 | Ellington |
| 2001/0050228 A1 | 12/2001 | Jaeger |

| | | | |
|---|---|---|---|
| 2001/0055544 | A1 | 12/2001 | Copp |
| 2002/0007249 | A1 | 1/2002 | Cranley et al. |
| 2002/0007687 | A1 | 1/2002 | Zimmermann et al. |
| 2002/0014236 | A1 | 2/2002 | Dittmann et al. |
| 2002/0017300 | A1 | 2/2002 | Hickle et al. |
| 2002/0026937 | A1 | 3/2002 | Mault |
| 2002/0034757 | A1 | 3/2002 | Cubicciotti |
| 2002/0068295 | A1 | 6/2002 | Madou et al. |
| 2002/0117176 | A1* | 8/2002 | Mantzaridis et al. .... 128/204.23 |
| 2002/0173729 | A1 | 11/2002 | Viertio-Oja et al. |
| 2002/0177232 | A1 | 11/2002 | Melker et al. |
| 2003/0004426 | A1 | 1/2003 | Melker et al. |
| 2003/0008407 | A1 | 1/2003 | Fu et al. |
| 2003/0059820 | A1 | 3/2003 | Vo-Dinh |
| 2003/0087239 | A1 | 5/2003 | Stanton et al. |
| 2003/0119065 | A1 | 6/2003 | Lin et al. |
| 2003/0139681 | A1 | 7/2003 | Melker et al. |
| 2003/0176804 | A1 | 9/2003 | Melker et al. |
| 2003/0185760 | A1 | 10/2003 | Lanza et al. |
| 2003/0216660 | A1 | 11/2003 | Ben-Oren et al. |
| 2004/0027246 | A1 | 2/2004 | Aguglia |
| 2004/0038386 | A1 | 2/2004 | Zesch et al. |
| 2004/0101477 | A1 | 5/2004 | Leyland-Jones |
| 2004/0162500 | A1 | 8/2004 | Kline |
| 2004/0236244 | A1 | 11/2004 | Allen et al. |
| 2005/0037374 | A1 | 2/2005 | Melker et al. |
| 2005/0054942 | A1 | 3/2005 | Melker et al. |
| 2005/0065446 | A1 | 3/2005 | Talton |
| 2005/0083527 | A1 | 4/2005 | Flaherty et al. |
| 2007/0167853 | A1* | 7/2007 | Melker et al. .................. 600/532 |

FOREIGN PATENT DOCUMENTS

| | | |
|---|---|---|
| DE | 29 902 593 | 8/1999 |
| EP | 0 370 151 A1 | 5/1990 |
| EP | 0 979 997 A1 | 2/2000 |
| GB | 829 409 A | 3/1960 |
| GB | 2 309 166 A | 7/1997 |
| GB | 2 329 245 A | 3/1999 |
| JP | 08 313 407 A | 11/1996 |
| JP | 09 196 915 A | 7/1997 |
| RU | 2 104 535 C1 | 2/1998 |
| WO | WO 87/02773 A1 | 5/1987 |
| WO | WO 92/10749 | 6/1992 |
| WO | WO 95/08113 A1 | 3/1995 |
| WO | WO 95/31718 | 11/1995 |
| WO | WO 98/57145 A1 | 12/1998 |
| WO | WO 99/12471 | 3/1999 |
| WO | WO 99/66304 | 12/1999 |
| WO | WO 00/25108 A1 | 5/2000 |
| WO | WO 00/67820 | 11/2000 |
| WO | WO 00/79243 A1 | 12/2000 |
| WO | WO 01/34024 | 5/2001 |
| WO | WO 01/93743 | 12/2001 |
| WO | WO 01/95971 | 12/2001 |
| WO | WO 02/17991 A2 | 3/2002 |
| WO | WO 02/079514 A1 | 10/2002 |
| WO | WO 03/016901 A1 | 2/2003 |
| WO | WO 03/045473 | 6/2003 |
| WO | WO 2004/037316 A | 5/2004 |
| WO | WO 2004/065404 A1 | 8/2004 |
| WO | WO 2005/033707 A | 4/2005 |
| WO | WO 2006/057816 | 6/2006 |

OTHER PUBLICATIONS

Hanson et al., "The use of a novel electronic nose to diagnose the presence of intrapulmonary infection," Anesthesiology, Sep. 1997, vol. 87, No. 3A, Abstract A269.

Hong, C. et al., "Carbon Nanotube-Enhanced Electrochemical DNA Biosensor for DNA Hybridization Detection", Anal. Bioanal. Chem., 2003, vol. 375, pp. 287-293.

Huang et. al., "Depth of anesthesia estimating & propofol delivery system", Aug. 1, 1996, http://www.rpi.edu/~royr/roy_descpyt.html.

Jayasena, "Aptamers: An Emerging Class of Molecules That Rival Antibodies in Diagnostics" Clinical Chemistry, 1999, vol. 45, No. 9, pp. 1628-1650.

Kenny, "Target-controlled infusions-pharmacokinetic and pharmacodynamic variations," http://www.anaesthesiologie.med.uni-erlangen.de/esctaic97/a_kenny.htm.

Kuipers et al, "First-pass lung uptake and pulmonary clearance of propofol," Anesthesiology, 1999, vol. 91, pp. 1780-1787.

Liebich et al. "Volatile Substances in Blood Serum: a Profile Analysis and Quantitative Determination," Journal of Chromatography, 1977, vol. 142, pp. 505-516.

Miller III, E. R. et al., "Association Between Cigarette Smoking and Lipid Peroxidation in a Controlled Feeding Study," Circulation, 1997, vol. 96, No. 4, pp. 1097-1101.

Mueller et al. "Experience in mass spectrometric identification in acute poisoning," Beitr. Diagn. Ther, Akuter. Intox., Vortr. Symp. 4th, 1982, pp. 126-134, Abstract Only.

Manolis, A., "The Diagnostic Potential of Breath Analysis," Clin. Chem., 1983, vol. 29, No. 1, pp. 5-15.

Mutlu, G. et at , "Collection and Analysis of Exhaled Breath Condensate in Humans," Am. J. Respir. Crit. Care Med., 2001, vol. 164, pp. 731-737.

U.S. Appl. No. 09/708,789, filed Nov. 8, 2000, Lampotang et al.

Brody et al., "Aptamers as therapeutic and diagnostic agents", Reviews in Molecular Biotechnology, 2000, vol. 74, pp. 5-13.

Brody et al., "The use of Aptamers in Large Arrays for Molecular Diagnostics", Molecular Diagnosis, 1999, vol. 4, No. 4, pp. 381-388.

Chandiok et al., "Screening for bacterial vaginosis: a novel application of artificial nose technology", Journal of Clinical Pathology, 1997, vol. 50, No. 9, pp. 790-791.

Dickinson, T. A. et al., "Current Trends in 'Artificial-Nose' Technology," Tib Tech, 1998, vol. 16, pp. 250-258.

Fang et al., "Detection of Organic Chemicals by SAW Sensor Array", Sensors and Actuators, 1999, vol. B56, pp. 155-157.

Fisher et al. "A man-portable chemical sniffer utilizing Novel Fluorescent polymers for detection of ultra-trace concentrations of explosives emanating from landmines," Nomadics Inc., 2000, pp. 1-10.

Frauendorf et al., "Detection of Small Organic Analytes by Fluorescing Molecular Switches", Bioorganic & Medicinal Chemistry 9, 2001, pp. 2521-2524.

Fujita et al., "A Simple method for detecting plasma propofol", Anesth. Analog, 2000, vol. 90, pp. 1452-1454.

Ganga-Zandzou, P.S. et al. "A 13C-urea breath test in children with Helicobacter pylori infection: validity of the use of a mask to collect exhaled breath sample," Acta. Paediatr., 2001, vol. 90, pp. 232-233.

Groves et al., "Analyzing organic vapors in exhaled breath using a surface acoustic wave sensor array with preconcentration: Selection and characterization of the preconcentrator adsorbent", Analytica Chimica Acta, 1998, pp. 131-143.

Pantarotto D. et al., "Synthesis, Structural Characterization, and Immunological Properties of Carbon Nanotubes Functionalized with Peptides", J. Am. Chem. Soc., 2003, vol. 125, pp. 6160-6164.

Parry et al., "Leg ulcer odour detection identified beta-haemolytic streptococcal infection," Journal of Wound Care, 1995, vol. 4, pp. 404-406.

Pavlou and Turner. "Sniffing out the truth: Clinical Diagnosis Using the Electronic Nose," Clin. Chem. Lab. Med., 2000, vol. 38, No. 2, pp. 99-112.

Perri, F. "Diagnosis of Helicobacter pylori infection: which is best? The urea breath test," Dig. Liver. Dis., 2000, vol. 32, Supp. 3, pp. S196-S198.

Pilar Kraman, "Prescription Drug Diversion," Trends Alert provided by the Council of State Government at www.csg.org, Apr. 2004.

Phillips, "Breath Tests in Medicine" Scientific American, 1992, pp. 52-57, XP001080159.

Rogers et al. "Fiber-optic biosensors based on total internal-reflection fluorescence," American Chemical Society, 1992, Ch. 13, pp. 165-173.

Stojanovic et al., "Aptamer-Based Folding Fluorescent Sensor for Cocaine" Journal of the American Chemistry Society, 2001, vol. 123, pp. 4928-4931.

Stuart, B. H. et al., "Studies of Adipocere Using Diffuse Reflectance Infrared Spectroscopy," Vibrational Spectroscopy, 2000, vol. 24, pp. 233-242.

Stubbs, D. D. et al., "Investigation of Cocaine Plumes Using Surface Acoustic Wave Immunoassay Sensors," Anal. Chem., 2003, vol. 75, pp. 6231-6235.

Tracqui, A. et al. "Systematic Toxicological Analysis Using HPLC/DAD," *Journal of Forensic Sciences*, 1995, vol. 40, No. 2, pp. 254-262.

United States Department of Justice, "Review of the Drug Enforcement Administration's (DEA) Control of the Diversion of Controlled Pharmaceuticals," Report No. I-2002-010 www.usdoj.gov/oig/inspection/DEA/0210/background.htm, Sep. 2002.

U.S. Food and Drug Administration, "FDA White Paper, Protecting the Public Health: FDA Pursues and Aggressive Enforcement Strategy," www.fda.gov/oc/whitepapers/enforce.html, Jun. 30, 2003.

U.S. Food and Drug Administration, "New FDA Initiative to Combat Counterfeit Drugs," www.fda.gov/oc/initiatives/counterfeit/backgrounder.html, Jul. 2, 2004.

Vass, A., "Beyond the Grave—Understanding Human Decomposition," *Microbiology Today*, Nov. 2001, vol. 28, pp. 190-192.

Vass, A. et al., "Decomposition Chemistry of Human Remains: A New Methodology for Determining the Postmortem Interval," *J. Forensic Sci.*, 2002, vol. 47, No. 3, pp. 542-553.

Vass, A. et al., "Detection of Buried Human Remains Using Bioreporter Fluorescence," U.S. Dept. of Energy Report, Y/NSP-726, 2001.

Wohltjen et al., "Determination of Partition Coefficients from Surface Acoustic Wave Vapor Senor Responses and Correlation with Gas—Liquid Chromatographic Partition Coefficients", *Anal. Chem.*, 1988, vol. 60, pp. 869-875.

Wohltjen et al., "Surface Acoustic Wave Devices for Chemical Analysis", *Anal. Chem.*, 1989, vol. 61, No. 11, pp. 704A-712A.

Wohltjen et al., "Vapor Detection with Surface Acoustic Wave Microsensors", *Chemical Sensors and Microinstrumentation*, 1989, pp. 157-175.

* cited by examiner

SYSTEM AND METHOD FOR MONITORING HEALTH USING EXHALED BREATH

CROSS-REFERENCE TO A RELATED APPLICATION

This application is a continuation application of co-pending U.S. patent application Ser. No. 11/301,911, filed Dec. 13, 2005; which is a continuation-in-part of co-pending International Application No. PCT/US2005/006355, filed Feb. 28, 2005, which is a continuation-in-part of U.S. patent application Ser. No. 10/788,501, filed Feb. 26, 2004, now abandoned which is a continuation-in-part of U.S. patent application Ser. No. 10/178,877, filed Jun. 24, 2002, now U.S. Pat. No. 6,981,947 which is a continuation-in-part of U.S. patent application Ser. No. 10/054,619, filed Jan. 22, 2002 now U.S. Pat. No. 7,104,963. All of the afore-mentioned applications are hereby incorporated by reference herein in their entirety, including any figures, tables, or drawings.

FIELD OF INVENTION

The present invention relates to non-invasive monitoring of substance/compound concentrations in blood; and more particularly, to a system and method for the determination of drug concentrations and endogenous compounds in blood utilizing a breath detection system.

BACKGROUND INFORMATION

Breath is a unique bodily fluid. Unlike blood, urine, feces, saliva, sweat and other bodily fluids, it is available on a breath to breath and therefore continuous basis. It is readily available for sampling non-invasively and because the lung receives all of the blood flow from the right side of the heart, measurements of analytes/compounds in breath correlate strongly and reproducibly with blood concentration. It is less likely to be associated with the transfer of serious infections than other bodily fluids and collection of samples is straightforward and painless.

Further, exhaled breath contains 100% humidity at 37° C. (body temperature), thus it can be considered an aerosol. If the temperature of the collected sample is maintained at 37° C. or higher it will remain in this state and can be treated as a gas for compounds that are insoluble in water or readily diffuse out of water. In this instance, sensors designed to work with gaseous media would be preferable. For compounds that are highly water soluble and likely to remain in solution, the exhaled breath sample can be collected as a condensate when cooled. This liquid can then be analyzed with sensors that are designed for liquid-based analyses. Compounds likely to be detectable in the gas phase typically are lipophilic (hydrophobic) such as the intravenous anesthetic agent, propofol, while compounds likely to be detected in the liquid phase are hydrophilic, such as glucose, lacetic acid and perhaps even electrolytes. Thus an exhaled breath sample can be handled to produce a gaseous matrix for certain compounds and sensors, and a liquid matrix for others. In instances where it is desirable to detect more than one compound (e.g., detection of hydrophilic and hydrophobic molecules in the breath), the sample can be split and a portion maintained as a gas and a portion condensed as a liquid.

An example of the unique characteristic of breath is the correlation between blood concentrations of drugs, both licit and illicit, and their concentration in the breath. The concentration of a drug in a patient's body is generally regulated both by the amount of drug ingested by the patient over a given time period, or the dosing regimen, and the rate at which the drug is metabolized and eliminated by the body.

Historically, pharmaceutical compositions were delivered to patients according to standard doses based on the patient's weight. In the early 1970s, it was discovered with epileptic patients that pharmaceutical treatment with dosages adjusted according to blood concentration of the drug was far more efficient and demonstrated better seizure control and fewer side effects than with dosages adjusted according to patient weight.

It is now generally accepted that with many medications, it is necessary to monitor the concentration in the blood stream in order to ensure optimal, therapeutic drug effect (therapeutic drug monitoring [TDM]). Medications are ineffective if blood concentration levels are too low. Moreover, certain medications are toxic to the body when concentration levels in the blood are too high. It would also be valuable to have a means for monitoring drug concentration in blood for medications that do not require constant monitoring. By monitoring blood serum drug levels, medication dosage can be individualized within a therapeutically effective range.

For example, patients prescribed tricyclic (or tetracyclic) antidepressants (TCAs) require frequent monitoring of blood levels. TCAs work by inhibiting serotonin and norepinephrine reuptake into the synaptic cleft. This group includes among its members the tricyclics: amitriptyline, imipramine, nortriptyline, and clomipramine, and the tetracyclics maprotiline and amoxapine. Although highly effective for the treatment of depression, TCAs have a high incidence of side effects, some of which may be life-threatening, especially when blood concentrations are too high. Consequently, TCAs have been largely replaced by serotonin reuptake inhibitors (SSRIs) for treatment of depression. In addition to the toxic effects of TCAs due to inhibition of sodium and potassium channels, which occurs primarily in the heart and brain, TCAs can also cause side effects due inhibition of norepinephrine reuptake and elevated norepinephrine levels. The latter can cause sedation, manic episodes, profuse sweating, palpitations, increased blood pressure, tachycardia, twitches and tremors of the tongue or upper extremities, and weight gain.

Although SSRIs are no more, or may actually be slightly less effective than TCAs, TCAs are less attractive because they are more toxic than SSRIs and pose a greater threat of overdose. A TCA overdose results in central nervous system and cardiovascular toxicity making the relative risk of death by overdose with a TCA 2.5 to 8.5 times that with the commercially available SSRI fluoxetine. The greater danger with TCA is that side effects, as well as constant blood sampling, will persuade the patient to discontinue treatment. Studies indicate that patients taking a classical antidepressant (TCA or MAOI) are three times as likely to drop out of treatment due to side effects and constant monitoring as patients taking SSRIs. Interestingly, recent studies have shown that some SSRIs (and a similar group of drugs—selective norepinephrine uptake inhibitors [SNRIs]) have a "cut-off" below which the drugs are far less effective than at doses above the "cut-off", but that this can only be determined by blood concentrations, not dosage due to large inter-patient variability. Thus, although drug manufacturers have tried to develop medications so "one dose fits all", TDM might be applied more readily and improve drug effectiveness while reducing side effects and overdose if a simple and efficacious method of determining blood concentrations were available. Exhaled breath drug monitoring holds such promise.

Thus, many therapeutically effective medications that require TDM are less likely to be prescribed by physicians in view of inconvenience in constant blood sampling and lack of patient compliance. Further, in the present era of cost-effective healthcare, considerations of prescription costs have become the primary issue for all aspects of laboratory operation. Individualization of drug therapy contributes to cost-effective patient management through detection and elimination of drug side effects; detection of unusual metabolism and adjustment of dosage based on individual metabolism; and detection of unusual metabolism and adjustment of dosage based on the effects on disease.

Drug level testing is especially important in patients being administered medications where the margin of safety between therapeutic effectiveness and toxicity is narrow (low therapeutic index). In addition to TCAs, other drugs such as procainamide or digoxin, which are used to treat arrhythmias and heart failure; dilantin or valproic acid, which are used to treat seizures; gentamicin or amikacin, which are antibiotics used to treat infections and lithium which is a mainstay of treatment for dipolar disease, are examples of medications having a narrow margin of safety and therapeutic effectiveness with administration.

Currently available tests for TDM are invasive, difficult to administer, frequently require the patient to be in a health care setting (versus home), and/or require an extended period of time for analysis. Such tests are generally complex, requiring a laboratory to perform the analysis. Healthcare providers' offices rarely possess appropriate testing technology to analyze blood samples and must therefore send the samples to an off-site laboratory or refer the patient to the laboratory to have their blood drawn, which results in an extended time period for analysis. In the process of transfer to and from a laboratory, there is a greater likelihood that samples will be lost or mishandled, or that the incorrect results are provided to the healthcare provider, which could be detrimental to the patient's health and well-being. Further, those on-site test devices that are presently available for assessing drug concentration levels in blood are expensive. Reference laboratories using sophisticated techniques such as gas chromatography-mass spectrometry typically conduct complex and expensive toxicological analyses to determine the quantity of a medication.

A further problem with present methods of TDM is that the concentration in the blood may not correlate with the concentration at the "effect site". It has been found that the concentration of drug in the blood may not directly reflect the concentrations at the cellular or receptor level, where drugs exert their biological effects. The pharmacodynamics and pharmacokinetics (PD/PK) of many drugs also exhibit wide inter- and intra-individual variation. The drug concentration at the site of action relates best with clinical responses; however, it is typically difficult or impossible to measure. Although plasma drug concentrations often provide an informative and feasible measurement for defining the pharmacodynamics of medications, they do not consistently provide an accurate report of drug disposition in a patient.

For medications appearing in breath, it appears that the concentration that appears in breath correlates best with the "free" drug in the body, that is, the drug available for the therapeutic effect, thus the concentration in exhaled breath is an excellent measure of the drug fraction that is most important for the healthcare provider to know in order to make informed decisions about dose regimens. Although the fraction of drug bound to protein and whole blood is essentially constant over a wide range of plasma and blood concentrations (i.e., free drug concentrations can be deduced from plasma and whole blood concentrations under normal circumstances) for the vast majority of subjects, various pathological circumstances can arise that make this correlation in a patient problematic (e.g., drug-drug interactions, massive blood loss and transfusion, protein losing syndromes, etc).

There are generally four processes by which drug disposition takes place: absorption, distribution, metabolism, and excretion. Absorption of a drug is generally dictated by route of drug administration (i.e., intravenous (IV), intramuscular (IM), subcutaneous (SC), topical, inhalation, oral, rectal, sublingual, etc.); drug factors (i.e., lipid solubility); as well as host factors (i.e., gastric emptying time). Alterations in drug absorption may affect the therapeutic effectiveness of the drug.

Factors related to drug distribution include body fat, protein binding, and membranes. Because lipid soluble drugs tend to dissolve in fat, drugs can build up to very high, potentially toxic, levels in a patient with a high percentage of body fat. There are several drugs available that have a high affinity for serum proteins. Protein binding limits the therapeutic effectiveness of the drug. Membranes such as the blood brain barrier (BBB) sometimes make it difficult for the drug to be properly distributed.

All tissues in the body can contribute to the metabolism of a drug. For example, the liver, kidney, lungs, skin, brain, and gut can all be involved in metabolizing a drug, although it most cases metabolism in the liver predominates. Physiologically, metabolism can increase the activity, decrease the activity, or have no effect on the activity of a drug. Because metabolism of a drug differs from one patient to another, the dosage required for a drug can differ from patient to patient.

Routes of drug elimination include the kidney, liver, gastrointestinal tract, lungs, sweat, lacrimal fluid, and milk. All of these processes (absorption, distribution, metabolism, and excretion), which can occur at varying times after drug administration, affect the level of pharmacologically effective drug in a patient. Thus, current methods for analyzing a blood sample to assess plasma drug concentrations only provides a snapshot for defining the pharmacodynamics of a drug and does not consistently provide an accurate report of drug disposition in a patient.

An example of the value of continuous or frequent breath monitor of drug concentrations is during anesthesia. Anesthesiologists use many sophisticated and expensive devices to monitor the vital signs of and to provide respiratory and cardiovascular support for patients undergoing surgical procedures. Such monitors provide the anesthesiologist with information about the patient's physiologic status and verify that the appropriate concentrations of delivered gases are administered.

Anesthesia can be achieved by using either inhalational or intravenous (IV) anesthetics, or combination of both. Inhalation anesthetics are substances that are brought into the body via the lungs and are distributed with the blood into the different tissues. The main target of inhalation anesthetics (or so-called volatile anesthetics) is the brain. Some commonly used inhalational anesthetics include enflurane, halothane, isoflurane, sevoflurane, desflurane, and nitrous oxide. Older volatile anesthetics include ether, chloroform, and methoxyflurane. Intravenous (IV) anesthetics frequently used clinically are barbiturates, opioids, benzodiazepines, ketamine, etomidate, and propofol. Currently, however, volatile anesthetics are seldom used alone. Rather, a combination of inhalation anesthetics and intravenous drugs are administered, in a process known as "balanced anesthesia." During administration of balanced anesthesia, for example, opioids are administered for analgesia, along with neuromuscular blockers for relaxation, anesthetic vapors for unconsciousness and benzodiazepines for amnesia.

Inhalational Anesthetics

With inhalation agents, the concentration of drug delivered is metered and the variation between patients in the depth of anesthesia resulting from known inhaled concentrations of agents is relatively narrow, permitting the anesthesiologist to confidently assume a particular level of anesthesia based on the concentration of anesthetic gas delivered.

Monitors used during the administration of inhalational anesthesia generally display inspired and exhaled gas concentrations. Most use side-stream monitoring wherein gas samples are aspirated from the breathing circuit through long tubing lines. A water trap, desiccant and/or filter may be used to remove water vapor and condensation from the sample. Gas samples are aspirated into the monitor at a low rate to minimize the amount of gas removed from the breathing circuit and, therefore, the patient's tidal volume. These gas monitors continuously sample and measure inspired and exhaled (end-tidal) concentrations of respiratory gases. The monitored gases are both the physiologic gases found in the exhaled breath of patients (oxygen, carbon dioxide, and nitrogen), as well as those administered to the patient by the anesthesiologist in order to induce and maintain analgesia and anesthesia.

There are a number of techniques to monitor respiratory gases, including mass spectroscopy, Raman spectroscopy, IR—light spectroscopy, IR—photo acoustics, piezoelectric (U.S. Pat. No. 4,399,686 to Kindlund), resonance, polarography, fuel cell, paramagnetic analysis, and magnetoacoustics. Infrared detector systems are most commonly used systems to monitor gas concentrations.

A major disadvantage of conventional gas monitors is that they only determine the concentrations of certain types of gases or a limited number of gases and most do not measure $N_2$ nor any medications delivered by other routes (i.e., intravenously). These monitors are also fragile, expensive and require frequent calibration and maintenance. For this reason, not all purchasers of anesthesia machines buy anesthesia gas monitors and therefore, rely on anesthesia gas vaporizers to control anesthetic gas concentration. Unfortunately, these vaporizers frequently go out of calibration and the anesthesiologist may administer too much or too little anesthesia.

Intravenous (IV) Anesthetics

Another method of providing anesthesia includes IV anesthetics. At present, a major impediment to the wider use of IV anesthetics, rather than inhaled anesthetics, has been the inability to precisely determine the quantity of drug required to provide a sufficient "depth of anesthesia" without accumulating an excessive amount.

Propofol, for example, is an agent that is widely used as a short acting IV anesthetic. Its physiochemical properties are hydrophobic and volatile. It is usually administered as a constant IV infusion in order to deliver and maintain a specific plasma concentration. Although the metabolism is mainly hepatic and rapid, there is significant inter-patient variability in the plasma concentration achieved with a known dose. However, the depth of anesthesia for a known plasma concentration is far less variable and it is therefore highly desirable to be able to evaluate plasma (or ideally free, unbound drug) concentrations in real time to accurately maintain anesthetic efficacy. ["A Simple Method for Detecting Plasma Propofol," Akihiko Fujita, M D, et al., Feb. 25, 2000, International Anesthesia Research Society]. The authors describe a means to measure plasma (free) rather than total propofol using headspace—GC with solid phase microextraction. This is preferable since plasma (free) propofol is responsible for the anesthetic effect. Prior methods of monitoring propofol concentration in blood include high-performance liquid chromatography (HPLC) and gas chromatography (GC). It has been reported that 97%-99% of propofol is bound with albumin and red blood cells after IV injection, and the remainder exists in blood as a free type. HPLC and GC detect the total propofol concentration, which does not correlate as well with the anesthetic effect as the plasma propofol level. Studies of exhaled breath propofol concentrations show an excellent correlation with plasma (free) concentration and therefore are likely to better predict the effect of the drug.

Propofol may also be monitored in urine. Metabolic processes control the clearance of propofol from the body, with the liver being the principal eliminating organ. ["First-pass Uptake and Pulmonary Clearance of Propofol," Jette Kuipers, et al., Anesthesiology, V91, No. 6, December 1999]. In a study, 88% of the dose of propofol was recovered in urine as hydroxylated and conjugated metabolites.

The aim of any dosage regimen in anesthesia is to titrate the delivery rate of a drug to achieve the desired pharmacologic effect for any individual patient while minimizing the unwanted toxic side effects. Certain drugs such as propofol, alfentanil and remifentanil have a close relationship between free blood concentration and effect; thus, the administration of the drug can be improved by basing the dosage regimen on the pharmacokinetics of the agent. [Kenny, Gavin, *Target-Controlled Infusions—Pharmacokinetics and Pharmacodynamic Variations*, http://www.anaesthesiologie.med.unierlangen.de/esctaic97/a_Kenny.htm]. Target controlled infusion (TCI) is one means for administering an IV anesthesia agent using a computer to control the infusion pump. Using a computer with a pharmacokinetic program permits control of a desired plasma concentration of an agent, such as propofol. The systems do not sample the blood in real-time, but use previously acquired population PD/PK parameters to provide a best estimate of the predicted blood concentration. However, even if TCI systems produced the exact target concentrations of blood concentration, it would not be possible to know if that concentration was satisfactory for each individual patient and for different points during the surgical procedure.

Among the technologies used to process and monitor electrical brain signal is BIS (Bispectral Index Monitor) monitoring of the EEG. It is an indirect monitor of depth of anesthesia. The BIS monitor translates EEG waves from the brain into a single number—depicting the depth of anesthesia on a scale from 1 to 100. In addition, neural networks have been used to classify sedation concentration from the power spectrum of the EEG signal. However, these technologies are costly and not entirely predictive.

Artificial neural networks have also been developed which use the patient's age, weight, heart rate, respiratory rate, and blood pressure to predict depth of anesthesia. The networks integrate physiological signals and extract meaningful information. Certain systems use mid-latency auditory evoked potentials (MLAEP) which are wavelet transformed and fed into an artificial neural network for classification in determining the anesthesia depth. [Depth of Anesthesia Estimating & Propofol Delivery System, by Johnnie W. Huang, et al., Aug. 1, 1996, http://www.rpi.edu/~royr/roy_descpt.html].

An apparatus and method for total intravenous anesthesia delivery is also disclosed in U.S. Pat. No. 6,186,977 to Andrews. This patent describes a method in which the patient is monitored using at least one of electrocardiogram (EKG), a blood oxygen monitor, a blood carbon dioxide monitor, inspiration/expiration oxygen, inspiration/expiration carbon dioxide, a blood pressure monitor, a pulse rate monitor, a respiration rate monitor, and a patient temperature monitor.

Combination Inhalational and Intravenous (IV) Anesthetics

As previously stated, anesthesia can be achieved by using either inhalational or IV anesthetics, or combination of both ("balanced anesthesia"). Monitoring techniques for inhalational and IV anesthesia differ because of the nature of the drug delivery. Monitors for inhalational anesthesia delivery generally comprise systems that monitor the breathing circuit. Monitors for IV anesthesia generally comprise physiologic monitoring of the patient rather than monitoring the concentration of the drug in the blood. Based on this bifurcation of monitoring systems, anesthesiologists must utilize separate systems when switching between drug delivery methods or when utilizing a combination of methods.

Accordingly, there is a need in the art for methods to improve therapeutic drug monitoring (such as IV and/or inhalational delivered anesthetics) and the monitoring of endogenous compounds related to health conditions that are non-invasive, speedy, and inexpensive in administration. There is also a need for a monitoring system capable of continuously monitoring drug concentration levels (to assess drug disposition) and of continuously monitoring endogenous compound levels (such as glucose levels in exhaled breath). Further, there is a need for non-invasive monitoring systems capable of being used at remote locations and/or non-laboratory settings to monitor the therapeutic efficacy of the drug or to assess patient health by monitoring endogenous compounds present in exhaled breath.

Other Applications for Intermittent or Continuous Breath Monitoring

In addition to monitoring blood concentrations of licit medications using exhaled breath either intermittently or continuously, exhaled breath measurements can be used to monitor a wide range of other compounds and correlate them with blood concentrations. For instance, breath can be used to determine whether an individual has used an illicit drug. Likewise, breath can be used to determine blood glucose concentrations, thus freeing diabetics from having to perform frequent blood sticks to determine their glucose concentrations. Breath glucose can also be measured continuously in the operating room during surgery and/or the intensive care units since tight glucose control has been shown to improve wound healing and reduce the incidence of post-operative infection.

The breath may also be an excellent media to diagnose acute and/or chronic "stress" in humans, which can occur in various settings (e.g., injured humans stressed due to disease, accidents, or military actions, etc.; or non-injured humans stressed due to extreme/excessive exercise or environments that require an extremely high level of vigilance such as the longterm operation of military aircraft under battlefield conditions). Various stress markers including those suggesting inflammation, which may appear in the breath, include but are not limited to concentrations of lacetic acid, ketones, cortisol, testosterone, ATP, ADP, AMP, adenosine, prostaglandins (e.g., PGF2a), leukotrienes, cytokines, interleukins, melatonin, 6-sulfatoxymelatonin, HIF-1α, HSP70 and myogenic regulatory factors.

For example, lacetic acid in blood is an indicator of the severity of shock (hypoperfusion) and numerous disease states. It is usually measured intermittently by drawing blood samples. Intermittent or continuous breath measurements of lacetic acid could revolutionize the care of critically ill patients in the operating room or intensive care unit. Numerous other compounds can also indicate disease states appear in breath. The ability to monitor these compounds in real-time, either intermittently or continuously without the delay of having to send specimens to a laboratory, could dramatically improve the care of hospitalized or even home care or ambulatory patients.

SUMMARY OF THE INVENTION

The present invention solves the needs in the art by providing a method and apparatus for non-invasive monitoring of substance/compound concentration in blood, and, more particularly to systems and methods for non-invasive monitoring of endogenous compound and/or therapeutic drug concentration in blood. The systems and methods of the present invention utilize sensors that can analyze a patient's exhaled breath components to detect, quantify, and/or trend concentrations of endogenous compound markers in exhaled breath, which correlate to the endogenous compound concentration in the patient's body, in particular in blood. Endogenous compound markers detectable in exhaled breath can be the endogenous compounds themselves or substances derived from the endogenous compounds (such as metabolites of endogenous compounds).

In other embodiments, systems and methods are provided for the detection, quantification, and trending of delivered therapeutic drug concentration utilizing sensors that can analyze a patient's exhaled breath components. Such systems and methods include: at least one supply of at least one therapeutic drug for delivery to a patient; and an expired gas sensor for analyzing the patient's breath for concentration of at least one drug or marker indicative of therapeutic drugs in the patient's bloodstream, wherein the sensor provides a signal to indicate marker concentration that corresponds to therapeutic drug concentration in the patient's bloodstream. The methods of the subject invention include the steps of measuring the concentration of one or more therapeutic markers in a patient's exhaled breath. These measured markers can then be used to quantify the concentration of therapeutic drug(s) in the patient's blood as well as trend the delivered drug, and ultimately determine the PD/PK of the drug.

In one embodiment, the subject invention contemplates administering to a patient a therapeutic drug, wherein the therapeutic drug contains a therapeutic drug marker that is detectable in exhaled breath by a sensor of the subject invention. In certain embodiments of the invention, the therapeutic drug marker is the therapeutic drug itself or a metabolite of the drug, which is detectable in exhaled breath. As contemplated herein, the blood concentration of the therapeutic drug and the exhaled concentration of the therapeutic drug marker are substantially proportional. By using a sensor of the subject invention for analyzing the concentration of a therapeutic drug marker in exhaled breath, which substantially corresponds to the blood concentration of a therapeutic drug, the present invention enables non-invasive, continuous monitoring of therapeutic drug blood concentration.

One particular application of the present invention is for predicting the depth of anesthesia utilizing a breath detection system. It has been shown that there is a good correlation between blood concentration of anesthetic agents (e.g., propofol) and depth of anesthesia. In a related embodiment, the present invention provides methods and apparatuses for the detection, quantitation, and trending of intravenous (IV) and/or inhalational delivered drug concentration utilizing a breath detection system.

Since there is no direct on-line method to continuously monitor blood concentration of agents, in that the blood and exhaled concentration are relatively proportional, the method of the present invention will provide a more predictive method to monitor depth of anesthesia by monitoring breath rather than blood.

In one embodiment, the method of the invention includes measuring both exhaled breath concentrations of IV and inhalational anesthetics, and also the circuit concentration of inhalational anesthetic gases. The method includes the steps of both measuring the circuit concentration and measuring the concentration of one or more components in the patient's exhaled breath. These measured components can then be used to quantitate the concentration of anesthetics in the circuit (such as halothane, isoflurane, sevoflurane, desflurane and enflurane) and to detect, quantitate, and trend the delivered drug, and ultimately determine depth of anesthesia.

The method of the present invention may also be used to monitor perflubron concentration. Emulsified perflubron is one of a class of compounds used to deliver oxygen in anemic patients as a substitute for hemoglobin.

In a preferred embodiment of the subject invention, a specific phase of the respiratory cycle, namely the end-tidal portion of exhaled breath, is sampled to detect the concentration of a therapeutic drug marker as a measure of drug concentration levels in blood.

In accordance with the subject invention, a sensor can be selected from a variety of systems that have been developed for use in collecting and monitoring exhaled breath components, particularly specific gases. For example, the sensor of the subject invention can be selected from those described in U.S. Pat. Nos. 6,010,459; 5,081,871; 5,042,501; 4,202,352; 5,971,937, and 4,734,777. Further, sensor systems having computerized data analysis components can also be used in the subject invention (i.e., U.S. Pat. No. 4,796,639).

Sensors of the subject invention can also include commercial devices commonly known as "artificial" or "electronic" noses or tongues to non-invasively monitor therapeutic drug blood concentration. Sensors of the subject invention can include, but are not limited to, metal-insulator-metal ensemble (IME) sensors, cross-reactive optical microsensor arrays, fluorescent polymer films, corona devices, surface enhanced Raman spectroscopy (SERS), semiconductor gas sensor technology, conductive polymer gas sensor technology, surface acoustic wave gas sensor technology, functionalized microcantilevers and immunoassays.

In certain embodiments, the systems of the subject invention include a reporting system capable of tracking marker concentration (remote or proximate) and providing the necessary outputs, controls, and alerts.

In one example, a sensor of the subject invention would be used either in a clinical setting or patient-based location during delivery of a therapeutic drug to monitor drug concentration in blood by measuring therapeutic drug marker concentration in patient exhaled breath. Moreover, exhaled breath detection using the systems and methods of the present invention may enable accurate evaluation of PD/PK for drug studies and/or in individual patients.

The preferred device of the present invention includes two parts: 1) the breathing circuit sensor and 2) the expired breath sensor. The breathing circuit sensor includes a sensor having a surface exposed to the gas stream and comprises a material selectively absorptive of a chemical vapor or group of vapors. The expired breath sensor includes a sensor having a surface exposed to the patient's breath and/or airway and also comprises a material selectively absorptive of a chemical vapor or group of vapors. These sensors are coupled to an analyzer(s) for producing an electrical signal indicative of the presence of the vapors. The analyzer is further operative to determine the approximate concentration of the vapors, display results, signal alarms, etc.

In one embodiment, the device detects a target substance (anesthetic gases and/or physiologic gases) in both the breathing circuit and in expired breath using the following components: (a) surface-acoustic wave sensor(s) capable of detecting the presence of the target substance, wherein the sensor responds to the target substance by a shift in the resonant frequency; (b) oscillator circuit(s) having the sensor as an active feedback element; (c) frequency counter(s) in communication with the oscillator circuit(s) to measure oscillation frequency which corresponds to resonant frequency of the sensor(s); and (d) a processor for comparing the oscillation frequency with a previously measured oscillation frequency of the target substance and determining presence and concentration of the target substance therefrom.

In another embodiment, the device detects a target marker (anesthetic gases and/or physiologic gases) in both the breathing circuit and in expired breath using the following components: (a) sensor(s) having an array of polymers capable of detecting the presence of the target substance, wherein the sensor(s) responds to the target substance by changing the resistance in each polymer resulting in a pattern change in the sensor array; (b) a processor for receiving the change in resistance, comparing the change in resistance with a previously measured change in resistance, and identifying the presence of the target substance from the pattern change and the concentration of the substance from the amplitude. The processor can include a neural network for comparing the change in resistance with a previously measured change in resistance to find a best match.

In another embodiment, the invention includes a method of monitoring a patient during administration of anesthesia wherein the patient is connected to a breathing circuit. In the method, a first sensor is exposed to inspired gases, wherein at least one inspired gas is an anesthetic agent; a second sensor is exposed to expired gases; one or more target substances is detected with the sensors; and concentration of the target substances is determined.

In another embodiment, the invention includes an anesthetic agent delivery system for delivering balanced anesthesia to a patient through a breathing circuit and an IV which includes: (1) an anesthetic gas supply having a controller for controlling the amount of volatile anesthetic agent provided by the supply to the breathing circuit; (2) an IV anesthetic agent supply having a controller for controlling the amount of IV anesthetic agent administered to the patient intravenously; (3) an inspired gas analyzer for analyzing the concentration of anesthetic gas in the breathing circuit; (4) an expired gas analyzer for analyzing the patient's breath for concentration of at least one substance indicative of anesthetic agent concentrations in the patient's bloodstream that provides at least one signal to indicate the anesthetic agent concentration delivered to the patient; and (5) a system controller connected to each of the anesthetic supplies which receives the signal and controls the amount of anesthetic agents administered based on the signal.

In still a further embodiment, the invention includes an apparatus for administering balanced anesthesia to a patient including: (1) at least one supply of at least one intravenous anesthetic agent; (2) intravenous delivery means for controllably delivering the intravenous anesthetic agent to the patent; (3) at least one supply of at least one inhalational anesthetic agent; (4) a breathing circuit for delivery of said inhalational anesthetic agent; (5) an inspired gas analyzer for analyzing gas in the breathing circuit for the inhalational agent; (6) an expired gas analyzer for analyzing the patient's breath for concentration of at least one substance indicative of anesthetic agents in the patient's bloodstream that provides a signal to indicate anesthetic agent concentration delivered to the patient; (7) a system controller connected to the intravenous delivery means which receives the signal and controls the amount of anesthetic agent based on the signal; and (8) a system controller connected to the breathing circuit which receives the signal and controls the amount of anesthetic agent based on the signal.

Another embodiment includes a device for detecting target substances in a breathing circuit including: (1) at least one surface-acoustic wave sensor capable of detecting the presence of the target substance in inspired and/or expired gas, wherein the sensor responds to the target substance by a shift in the resonant frequency; (2) an oscillator circuit having the sensor as an active feedback element; (3) a frequency counter in communication with the oscillator circuit to measure oscillation frequency which corresponds to resonant frequency of the sensor; and (4) a processor for comparing the oscillation frequency with a previously measured oscillation frequency of the target substance and determining presence and concentration of the target substance therefrom.

Another embodiment includes a device for detecting target substances in a breathing circuit including: (1) a sensor having an array of polymers capable of detecting the presence of the target substance in inspired and/or expired gas, wherein the sensor responds to the target substance by changing the resistance in each polymer resulting in a pattern change in the sensor array; (2) a processor for receiving the change in resistance, comparing the change in resistance with a previously measured change in resistance, and identifying the presence of the target substance from the pattern change and the concentration of the substance from the amplitude.

Moreover, sensing antibiotics with the exhaled breath detection method of the present invention, would allow for use of the method as a surrogate for blood antibiotic concentration. This would also be true for a wide range of medications for which blood concentration would be valuable. Exhaled breath detection using the method of the present invention may also evaluate PD/PK for both drug studies and in individual patients. Moreover, it may be used to sense endogenous compounds such as glucose, ketones, lacetic acid and electrolytes, which are normally found in blood.

The invention also includes a method of determining the rate of washout of a target substance (such as anesthetic gases or other drugs) by (a) obtaining a sample of expired breath at a first interval; (b) analyzing the sample with sensor technology to determine the concentration of the substance; (c) obtaining at least one additional sample of expired breath at a later interval; (d) analyzing said additional sample with sensor technology to determine the concentration of said substance; and (e) comparing the concentration of the first sample with the concentration of additional samples to determine rate of washout of the target substance.

Therefore, it is an object of the present invention to non-invasively monitor therapeutic drug blood or endogenous compound concentration by monitoring the concentration of therapeutic drug marker or endogenous compound marker, respectively, present in exhaled breath using sensors that analyze markers in exhaled breath.

In one embodiment of the invention, monitoring of therapeutic drug marker and/or endogenous compound marker concentration is conducted continuously using a system of the invention. In another embodiment of the invention, monitoring of therapeutic drug marker and/or endogenous compound marker concentration is conducted intermittently using a system of the invention.

Another object of the present invention is to non-invasively monitor substance concentration (such as endogenous compound blood concentration) by monitoring substance or substance marker concentrations in exhaled breath using sensors that analyze exhaled breath components. Exhaled breath detection using the method of the present invention may be used to sense endogenous compounds such as glucose, ketones, lacetic acid, and electrolytes that are normally found in blood. These compounds could be monitored intermittently or continuously in a wide range of environments. Small handheld portable equipment could be used by patients in the home, at work, in nursing homes or while they are ambulatory, while other devices could be designed for continuous monitoring in the operating room, intensive care units and in other areas of hospitals or other healthcare facilities such as clinics, doctors offices where this capability would be valuable.

A resulting advantage of the subject invention is the ability to monitor such substance and/or therapeutic drug concentration in a more cost effective and frequent manner than current methods, which involve drawing blood samples and transferring the blood samples to a laboratory facility for analysis. In addition, the subject invention enables the user to immediately and continuously monitor therapeutic drug and/or endogenous compound concentration levels in a patient's blood stream to monitor patient health, whether in a clinical setting or via known forms of communication if the patient is located at a remote location. The systems and methods of the subject invention can be used in place of the invasive practice of drawing blood to measure concentration.

The invention will now be described, by way of example and not by way of limitation, with reference to the accompanying sheets of drawings and other objects, features and advantages of the invention will be apparent from the following detailed disclosure and from the appended claims.

DETAILED DESCRIPTION OF THE INVENTION

Figure 1:
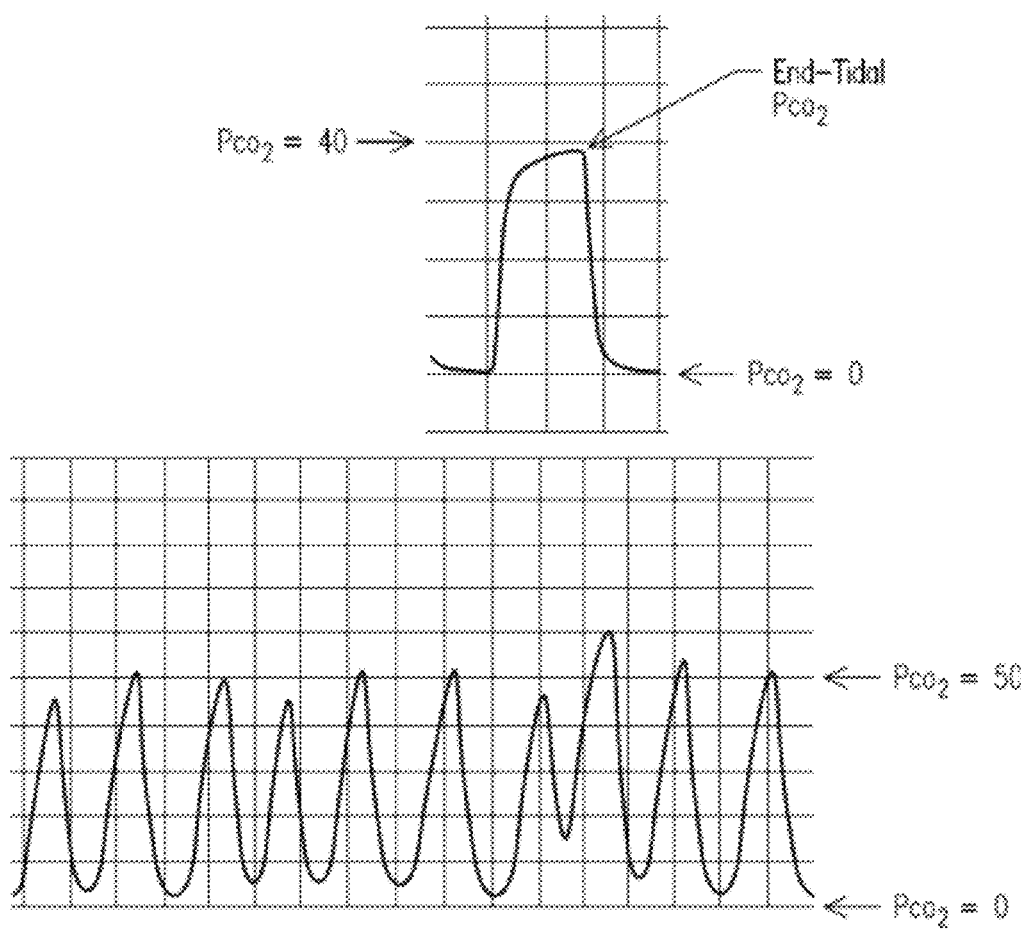
FIG. 1 shows a capnogram of a single respiratory cycle and a capnogram of several breaths from a patient with obstructive lung disease.

The present invention provides systems and methods for non-invasive monitoring of substances in blood by analyzing a patient's exhaled breath components. Substances in blood that can be monitored by analyzing exhaled breath components include, but are not limited to, endogenous compounds, such as glucose, ketones, lacetic acid, prostaglandins, leukotrienes, cortisol, and electrolytes, and therapeutic drugs, including IV and/or inhalation anesthetics for detecting the depth of anesthesia and a wide range of licit and illicit drugs.

In certain embodiments, the breath concentration of at least one endogenous compound marker is analyzed using sensor technology. The endogenous compound marker can be the endogenous compound itself or derived from the endogenous compound, such as a metabolite of the endogenous compound. According to the present invention, the concentration of an endogenous compound marker in breath is proportionate to the concentration of the corresponding endogenous compound in blood. Thus, based on the breath concentration of endogenous compound markers, the concentration of the corresponding endogenous compounds in a patient can be non-invasively and efficiently assessed.

Definitions

As used herein, the term "therapeutic drug" or "drug" refers to a substance used in the diagnosis, treatment, or prevention of a disease or condition, wherein the concentration of the therapeutic drug in a patient's blood stream must be monitored to ensure the therapeutic drug level is within a clinically effective range. A therapeutic drug of the present invention includes anesthetic agents.

Throughout this disclosure, a "marker" is defined as a substance that is detected by means of its physical or chemical properties using a sensor of the subject invention. According to the subject invention, an endogenous compound marker is either the endogenous compound itself or a compound derived directly from the endogenous compound (such as a metabolite of the endogenous compound). Therapeutic drug markers are the therapeutic drug itself, or derived either directly from the therapeutic drug (such as a metabolite) or from an additive combined with the therapeutic drug prior to administration. Such therapeutic drug markers preferably include olfactory markers (odors) as well as other substances and compounds, which may be detectable by sensors of the subject invention.

Halogenated compounds (i.e. fluorinated drugs or markers) hold particular promise as they are readily highly volatile, safe for human consumption at doses required, and are readily detected in exhaled breath with several types of portable Freon leak detectors. Some of these compounds are used as propellants for delivery of drugs via the pulmonary route, such as metered dose inhalers and therefore are known to be safe and are FDA approved. The technologies most often used to detect Freon leaks include: Negative Ion Capture, Heated Sensor/Ceramic Semiconductor, Infrared Absorption, and TIF TIFXP-1A Negative Corona Leak Detector. Many drugs are fluorinated and metabolites are often extremely volatile and detectable in exhaled breath. Numerous such compounds are available that could be used as markers and could be added as excipients during the manufacture of drugs A "patient," as used herein, describes an organism, including mammals, from which exhaled breath samples are collected in accordance with the present invention. Mammalian species that benefit from the disclosed systems and methods for therapeutic drug monitoring include, and are not limited to, apes, chimpanzees, orangutans, humans, monkeys; and domesticated animals (e.g., pets) such as dogs, cats, mice, rats, guinea pigs, and hamsters.

According to the subject invention, substances detectable in exhaled breath using the systems and methods of the invention include those that may be found in breath gas, breath condensate (liquid phase), respiratory droplet, breath evaporate, water vapor, and/or bronchial or alveolar aerosols.

The term "pharmacodynamics," as used herein, refers to the interaction (biochemical and physiological) of a therapeutic drug with constituents of a patient body as well as the mechanisms of drug action on the patient body (i.e., drug effect on body).

As used herein, the term "pharmacokinetics" refers to the mathematical characterization of interactions between normal physiological processes and a therapeutic drug over time (i.e., body effect on drug). Certain physiological processes (absorption, distribution, metabolism, and elimination) will affect the ability of a drug to provide a desired therapeutic effect in a patient. Knowledge of a drug's pharmacokinetics aids in interpreting drug blood stream concentration and is useful in determining pharmacologically effective drug dosages.

"Concurrent" administration, as used herein, refers to the administration of a therapeutic drug marker suitable for use with the systems and methods of the invention (administration of a therapeutic drug) for monitoring therapeutic drug levels in blood stream. By way of example, a therapeutic drug marker can be provided in admixture with a therapeutic drug, such as in a pharmaceutical composition; or the marker and therapeutic drug can be administered to a patient as separate compounds, such as, for example, separate pharmaceutical compositions administered consecutively, simultaneously, or at different times. Preferably, if the marker and the therapeutic drug are administered separately, they are administered within sufficient time from each other so that the concentration of the marker in exhaled breath is an accurate indicator of the concentration of therapeutic drug in the blood stream.

The term "aptamer," as used herein, refers to a non-naturally occurring oligonucleotide chain that has a specific action on a therapeutic drug marker. Aptamers include nucleic acids that are identified from a candidate mixture of nucleic acids. In a preferred embodiment, aptamers include nucleic acid sequences that are substantially homologous to the nucleic acid ligands isolated by the SELEX method. Substantially homologous is meant a degree of primary sequence homology in excess of 70%, most preferably in excess of 80%.

The "SELEX™" methodology, as used herein, involves the combination of selected nucleic acid ligands, which interact with a target marker in a desired action, for example binding to an olfactory marker, with amplification of those selected nucleic acids. Optional iterative cycling of the selection/amplification steps allows selection of one or a small number of nucleic acids, which interact most strongly with the target marker from a pool, which contains a very large number of nucleic acids. Cycling of the selection/amplification procedure is continued until a selected goal is achieved. The SELEX methodology is described in the following U.S. patents and patent applications: U.S. patent application Ser. No. 07/536,428 and U.S. Pat. Nos. 5,475,096 and 5,270,163.

As used herein, the term "pharmaceutically acceptable carrier" means a carrier that is useful in preparing a pharmaceutical composition that is generally compatible with the other ingredients of the composition, not deleterious to the patient, and neither biologically nor otherwise undesirable, and includes a carrier that is acceptable for veterinary use as well as human pharmaceutical use. "A pharmaceutically acceptable carrier" as used in the specification and claims includes both one and more than one such carrier.

Breath Sampling

Generally, the exhalation gas stream comprises sequences or stages. At the beginning of exhalation there is an initial stage, the gas representative thereof coming from an anatomically inactive (deadspace) part of the respiratory system, in other words, from the mouth and upper respiratory tracts. This is followed by a plateau stage. Prior to the plateau stage, the gas is a mixture of deadspace and metabolically active gases. During the plateau phase, which comprises the last portion of the exhaled breath, nothing but deep lung gas, so-called alveolar gas is present. This gas, which comes from the alveoli, is termed end-tidal gas.

According to the present invention, exhaled gas from any specific phase of the respiratory cycle can be sampled to detect for the presence of target markers as indicators of therapeutic drug and/or endogenous compound concentration in the patient. For example, sensor technology as described herein can be applied to exhalation samples drawn from the initial phase, or the end-tidal (late plateau) phase.

Technology used for end-tidal component monitoring (such as $CO_2$ sensors, $O_2$ sensors, and NO sensors) can be used to determine when or at what stage the sample is collected. Known methods for airway pressure measurements or for monitoring gas flow afford other means of collecting samples at the appropriate phase of the respiratory cycle. In a preferred embodiment, the exhaled breath sample is collected at end-tidal breathing.

Single or multiple samples collected by the known in-line (or mainstream) sampling method are preferable, but if sensor acquisition time is reduced, side stream sampling may be used. With in-line sampling, a sensor of the subject invention is placed proximal to the ET tube directly in the gas stream. In the latter, samples are collected through an adapter at the proximal end of an endotracheal (ET) tube and drawn through thin bore tubing to a sensor of the subject invention. In certain embodiments that use in-line sampling, the sensor is placed in a sampling chamber positioned within the patient's gas stream. Alternatively to sample end-tidal gas, samples can be taken throughout the exhalation phase of respiration and an average value determined and correlated with blood concentration. Depending on the sample size and sensor response time, exhaled gas may be collected on successive cycles.

Referring now to FIG. 1, the upper frame demonstrates a capnogram of a single respiratory cycle. For accurate blood level correlation, samples are taken at the point labeled "end-tidal $PCO_2$," which reflects the $CO_2$ concentration in the lung. The lower frame shows a capnogram of several breaths from a patient with obstructive lung disease. Again the end-tidal sample correlated best with blood concentration.

In one embodiment, a VaporLab™ brand instrument is used to collect and analyze exhaled breath samples. The VaporLab™ instrument is a hand-held, battery powered SAW-based chemical vapor identification instrument suitable for detecting components in exhaled breath samples in accordance with the present invention. This instrument is sensitive to volatile and semi-volatile compounds using a high-stability SAW sensor array that provides orthogonal vapor responses for greater accuracy and discrimination. In a related embodiment, this instrument communicates with computers to provide enhanced pattern analysis and report generation. In a preferred embodiment, this instrument includes neural networks for "training" purposes, i.e., to remember chemical vapor signature patterns for fast, "on-the-fly" analysis.

In another embodiment, samples are collected at the distal end of an ET tube through a tube with a separate sampling port. This may improve sampling by allowing a "cleaner— (less deadspace)" sample during each respiratory cycle.

In certain instances, the concentration of a therapeutic drug in a patient body is regulated by the amount of the drug administered over a given time period and the rate at which the agent is eliminated from the body (metabolism). The present invention provides the steps of administering a therapeutic drug to a patient and analyzing patient exhaled breath for concentration of therapeutic drug markers such as unbound substances, active metabolites, or inactive metabolites associated with the therapeutic drug, after a suitable time period. In certain embodiments of the subject invention, the marker concentration indicates a characteristic of metabolism of the drug in the patient.

Methods of the subject invention may further include the use of a flow sensor to detect starting and completion of exhalation. The method further includes providing results from the analysis and communicating to the user or patient the blood concentration of the therapeutic drug. In a preferred embodiment, results from analysis can be communicated immediately upon sampling exhaled gases.

In certain embodiments, the subject invention enables the immediate monitoring of therapeutic drug levels in a patient's blood stream. As contemplated herein, immediate monitoring refers to sampling and analysis of exhaled gases from a patient for target markers substantially completely within a short time period following administration of a therapeutic drug (i.e., generally within a few minutes to about 24 hours).

Alternatively, in certain instances, a specific period of time must progress before a therapeutic drug concentration level in the blood stream can be detected. Accordingly, a system and/or method of the invention can be provided to a patient taking a therapeutic drug for intermittent or continuous monitoring of therapeutic drug concentrations (or endogenous compound markers) in the blood stream. In certain embodiments, the monitoring system and method of the subject invention can be administered to a patient taking a therapeutic drug on an hourly, daily, weekly, monthly, or even annual basis. Further, additional monitoring can be administered to a patient when an additional therapeutic drug is prescribed.

Moreover, a CPU may be provided as a data processing/control unit for automatically detecting the signal from the flow sensor to control sampling of exhaled breath. The CPU may further provide to the user/patient the appropriate dosage of the therapeutic drug to be delivered based on analysis of trends in therapeutic drug blood concentration. In certain embodiments, where the depth of anesthesia is to be monitored and controlled, the CPU may further provide the analysis and control of the infusion pump or other administering means for anesthetic agents.

Depending on the mode of therapeutic drug administration, the present invention provides means for automatically adjusting and administering the appropriate dosage of a therapeutic drug, based on blood concentration levels, to a patient. In certain embodiments, a CPU is provided for analysis and control of dosage adjusting and administering means. In one embodiment in which a therapeutic drug is delivered intravenously, an infusion pump is used, wherein the CPU provides analysis and control of the infusion pump.

Concentration in the blood of therapeutic drug markers, as measured by breath analysis in accordance with the present invention, may indicate when the patient is receiving a high dose (i.e., toxic dose), a low dose (i.e., ineffective dose), or effective (i.e., appropriate) dose of the therapeutic drug. Even if there is wide variation in the metabolism or response to the therapeutic drug, knowledge of the exhaled breath concentration allows the user to know if the drug is accumulating in the blood, possibly leading to dangerously toxic levels of the drug, or that the concentration is falling, possibly leading to an inadequate dose of the drug. Monitoring changes in therapeutic drug blood concentration in accordance with the subject invention are, therefore, useful.

In another embodiment, the exhalation air is measured for marker (such as endogenous compound, therapeutic drug, free agent, and/or metabolite) concentration either continuously or intermittently/periodically. From the exhalation air is extracted at least one measured marker concentration value. Numerous types of breath sampling apparatuses can be used to carry out the method of the present invention.

In one embodiment, the breath sampling apparatus includes a conventional flow channel through which exhalation air flows. The flow channel is provided with a sensor of the subject invention for measuring marker concentration. Furthermore, necessary output elements may be included with the breath sampling apparatus for delivering at least a measured concentration result to the user, if necessary.

Figure 2:
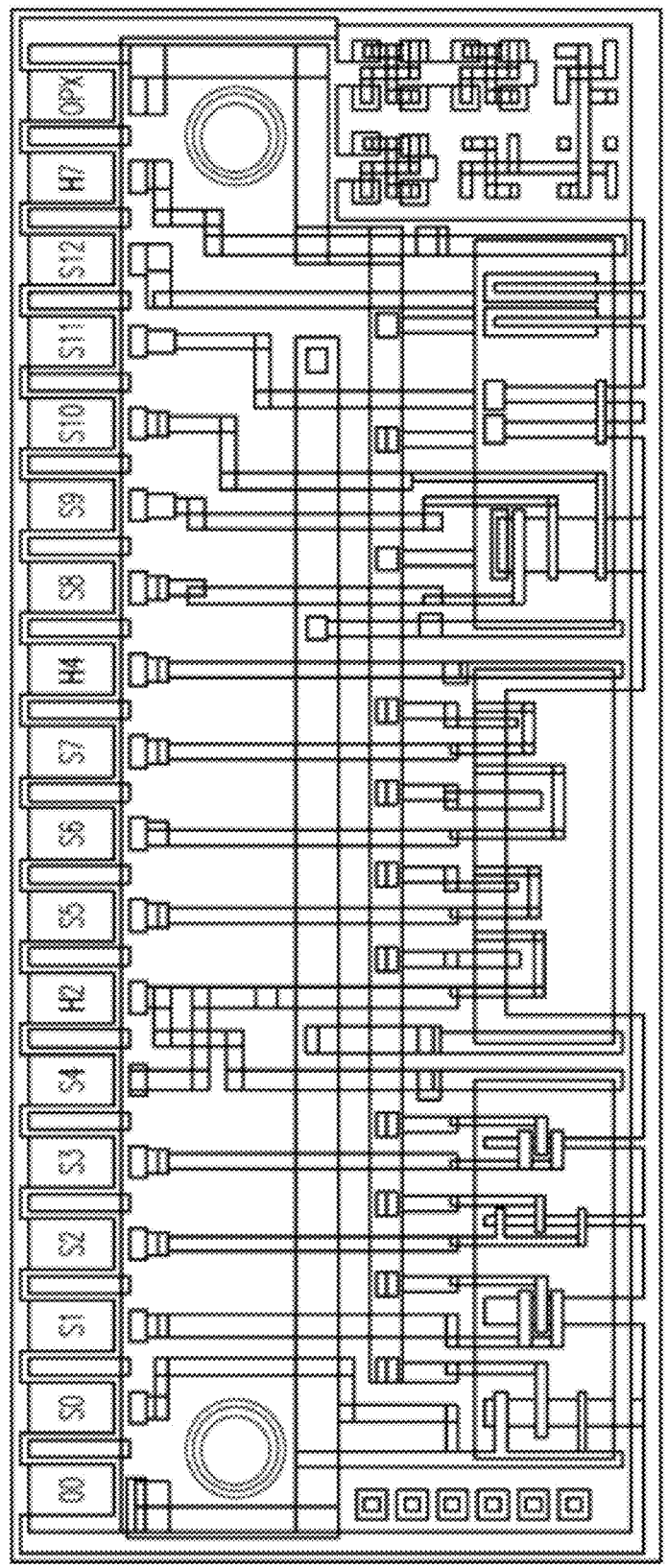
FIG. 2 shows a gas sensor chip, which may be utilized as the sensor for the present invention.

An alarm mechanism may also be provided. An instrument of similar type is shown in FIGS. 1 and 2 of U.S. Pat. No. 5,971,937 incorporated herein by reference.

In another embodiment, once the level of concentration is measured, it is given numerical value (for example, 50 on a scale of 1 to 100). Should the concentration fall below that value, the new value would be indicative of a decrease in concentration. Should the concentration increase beyond that value, the new value would be indicative of an increase in concentration. This numerical scale would allow for easier monitoring of changes in concentration. The numerical scale would also allow for easier translation into control signals for alarms, outputs, charting, and control of external devices (e.g., infusion pump). The upper and lower limits could be set to indicate thresholds such as from ineffective to dangerous therapeutic drug levels.

Sensor Technology

The invention preferably utilizes gas sensor technology, such as commercial devices known as "artificial" or "electronic" tongues or noses, to non-invasively monitor marker concentration in exhaled breath (FIG. 2). Electronic noses have been used mostly in the food, wine, and perfume industry where their sensitivity makes it possible to distinguish between odorous compounds. For example, electronic noses have been useful in distinguishing between grapefruit oil and orange oil in the perfume industry and identify spoilage in perishable foods before the odor is evident to the human nose.

In the past, there was little medical-based research and application of these artificial/electronic tongues and noses. However, recent use has demonstrated the power of this non-invasive technique. For example, electronic noses have been used to determine the presence of bacterial infection in the lungs by analyzing the exhaled gases of patients for odors specific to particular bacteria (Hanson C W, Steinberger H A, "The use of a novel electronic nose to diagnose the presence of intrapulmonary infection," *Anesthesiology,* 87(3A): Abstract A269, (1997)). Also, a genitourinary clinic has utilized an electronic nose to screen for, and detect bacterial vaginosis, with a 94% success rate after training (Chandiok S, et al., "Screening for bacterial vaginosis: a novel application of artificial nose technology,"*Journal of Clinical Pathology,* 50(9):790-1 (1997)). Specific bacterial species can also be identified with the electronic nose based on special odors produced by the organisms (Parry A D et al., "Leg ulcer odor detection identifies beta-haemolytic streptococcal infection," *Journal of Wound Care,* 4:404-406 (1995)).

A number of patents which describe gas sensor technology that can be used in the subject invention include, but are not limited to, the following: U.S. Pat. Nos. 5,945,069; 5,918, 257; 4,938,928; 4,992,244; 5,034,192; 5,071,770; 5,145,645; 5,252,292; 5,605,612; 5,756,879; 5,783,154; and 5,830,412. Other sensors suitable for the present invention include, but are not limited to, metal-insulator-metal ensemble (MIME) sensors, cross-reactive optical microsensor arrays, fluorescent polymer films, surface enhanced raman spectroscopy (SERS), diode lasers, selected ion flow tubes, metal oxide sensors (MOS), non-dispersive infrared spectrometer, bulk acoustic wave sensors, colorimetric tubes, functionalized microcantilevers and infrared spectroscopy.

Recent developments in the field of detection that can also be used as sensor for the subject invention include, but are not limited to, gas chromatography, semiconductive gas sensors, mass spectrometers (including proton transfer reaction mass spectrometry), and infrared (IR) or ultraviolet (UV) or visible or fluorescence spectrophotometers (i.e., non-dispersive infrared spectrometer). For example, with semiconductive gas sensors, markers cause a change in the electrical properties of semiconductor(s) by making their electrical resistance vary, and the measurement of these variations allows one to determine the concentration of marker(s). In another example, gas chromatography, which consists of a method of selective detection by separating the molecules of gas compositions, may be used as a means for analyzing markers in exhaled breath samples.

In accordance with the subject invention, sensors for detecting/quantifying markers utilize a relatively brief detection time of around a few seconds. Other recent gas sensor technologies contemplated by the present invention include apparatuses having conductive-polymer gas-sensors ("polymeric"), aptamer biosensors, amplifying fluorescent polymer (AFP) sensors, and apparatuses having surface-acoustic-wave (SAW) gas-sensors.

The conductive-polymer gas-sensors (also referred to as "chemoresistors") have a film made of a conductive polymer sensitive to the molecules of odorous substances. On contact with target marker molecules, the electric resistance of the sensors changes and the measurement of the variation of this resistance enables the concentration of the markers to be determined. An advantage of this type of sensor is that it functions at temperatures close to room temperature. Different sensitivities for detecting different markers can be obtained by modifying or choosing an alternate conductive polymer.

Polymeric gas sensors can be built into an array of sensors, where each sensor is designed to respond differently to different markers and augment the selectivity of the therapeutic drug markers. For example, a sensor of the subject invention can comprise of an array of polymers, (i.e., 32 different polymers) each exposed to a marker. Each of the individual polymers swells differently to the presence of a marker, creating a change in the resistance of that membrane and generating an analog voltage in response to that specific marker ("signature"). The normalized change in resistance can then be transmitted to a processor to identify the type, quantity, and quality of the marker based on the pattern change in the sensor array. The unique response results in a distinct electrical fingerprint that is used to characterize the marker. The pattern of resistance changes of the array is diagnostic of the marker in the sample, while the amplitude of the pattern indicates the concentration of the marker in the sample.

Responses of polymeric gas sensors to target markers can be fully characterized using a combination of conventional gas sensor characterization techniques. For example, the sensor can be attached to a computer. The results can be displayed on the computer screen, stored, transmitted, etc. A data analyzer can compare a pattern of response to previously measured and characterized responses from known substances. The matching of those patterns can be performed using a number of techniques, including neural networks. By comparing the analog output from each of the 32 polymers to a "blank" or control, for example, a neural network can establish a pattern that is unique to that substance and subsequently learns to recognize that substance. The particular resistor geometries are selected to optimize the desired response to the particular substance being sensed. In one embodiment, the sensor of the present invention is a self-calibrating polymer system suitable for liquid or gas phase biological solutions for detecting a variety of target markers simultaneously.

Another sensor of the invention can be provided in the form of an aptamer. In one embodiment, the SELEX™ (Systematic Evolution of Ligands by EXponential enrichment) methodology is used to produce aptamers that recognize therapeutic drug markers with high affinity and specificity. Aptamers produced by the SELEX methodology have a unique sequence and the property of binding specifically to a desired marker. The SELEX methodology is based on the insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. According to the subject invention, therapeutic drug markers of any size or composition can thus serve as targets for aptamers. See also Jayasena, S., "Aptamers: An Emerging Class of Molecules val Antibodies for Diagnostics," *Clinical Chemistry*, 45:9, 1628-1650 (1999).

Aptamer biosensors can be utilized in the present invention for detecting the presence of markers in exhaled breath samples. In one embodiment, aptamer sensors are composed of resonant oscillating quartz sensors that can detect minute changes in resonance frequencies due to modulations of mass of the oscillating system, which results from a binding or dissociation event (i.e., binding with a target therapeutic drug marker).

Similarly, molecular beacons (MB) and molecular beacon aptamers (MBA) employ fluorescence resonance energy transfer based methods to provide fluorescence signal increases in the presence of particular target sequences. See also, Stojanovic, Milan N., de Prada, Paloma, and Landry, Donald W., "Aptamer-Based Folding Fluorescent Sensor for Cocaine" J. Am. Chem. Soc. 2001, 123, 4928-4931 (2001); Jayasena, Sumedha D., "Aptamers: An Emerging Class of Molecules val Antibodies of Diagnostics, Clinical Chemistry 45:9, 1628-1650 (1999).

Amplifying fluorescent polymer (AFP) sensors may be utilized in the present invention for detecting the presence of therapeutic drug markers and/or endogenous compound markers in exhaled breath samples. AFP sensors are extremely sensitive and highly selective chemosensors that use amplifying fluorescent polymers. When target markers bind to thin films of the polymers, the fluorescence of the film decreases. A single molecule binding event quenches the fluorescence of many polymer repeat units, resulting in an amplification of the quenching. The binding of markers to the film is reversible, therefore the films can be reused.

Surface-acoustic-wave (SAW) sensors oscillate at high frequencies and generally have a substrate, which is covered by a chemoselective material. In SAW sensors, the substrate is used to propagate a surface acoustic wave between sets of interdigitated electrodes (i.e., to form a transducer). The chemoselective material is coated on the transducer. When a marker interacts with the chemoselective material coated on the substrate, the interaction results in a change in the SAW properties, such as the amplitude of velocity of the propagated wave. The detectable change in the characteristic wave is generally proportional to the mass load of the marker(s) (i.e., concentration of the marker in exhaled breath, which corresponds to the concentration of the therapeutic drug and/or endogenous compound in the blood stream).

Certain embodiments of the invention use known SAW devices, such as those described in U.S. Pat. Nos. 4,312,228 and 4,895,017, and Groves W. A. et al., "Analyzing organic vapors in exhaled breath using surface acoustic wave sensor array with preconcentration: Selection and characterization of the preconcentrator adsorbent," *Analytica Chimica Acta*, 371:131-143 (1988). Other types of chemical sensors known in the art that use chemoselective coating applicable to the operation of the present invention include bulk acoustic wave (BAW) devices, plate acoustic wave devices, interdigitated microelectrode (IME) devices, optical waveguide (OW) devices, electrochemical sensors, and electrically conducting sensors.

In one embodiment, the sensor of the invention is based on surface acoustic wave (SAW) sensors. The SAW sensors preferably include a substrate with piezoelectric characteristics covered by a polymer coating, which is able to selectively absorb target markers. SAW sensors oscillate at high frequencies and respond to perturbations proportional to the mass load of certain molecules. This occurs in the vapor phase on the sensor surface.

In a related embodiment, the sensor of the invention is based on a SAW sensor of Stubbs, D. et al. (see Stubbs, D. et al., "Investigation of cocaine plumes using surface acoustic wave immunoassay sensors," *Anal Chem.*, 75(22):6231-5 (November 2003) and Stubbs, D. et al., "Gas phase activity of anti-FITC antibodies immobilized on a surface acoustic wave resonator device," *Biosens Bioelectron*, 17(6-7):471-7 (2002)). For example, the sensor of the subject invention can include a two-port resonator on ST-X quartz with a center frequency of 250 MHz. On the cut quartz, a temperature compensated surface acoustic wave (SAW) is generated via an interdigital transducer. Antibodies specific to a target marker are then attached to the electrodes (i.e., 1.5 micron wide) on the sensor device surface via protein cross linkers. In the vapor phase on the sensor surface, when target markers are present, a change in frequency occurs to alert the user that a target marker has been recognized.

In a related embodiment, the SAW sensor is connected to a computer, wherein any detectable change in frequency can be detected and measured by the computer. In a preferred embodiment, an array of SAW sensors (4-6) is used, each coated with a different chemoselective polymer that selectively binds and/or absorbs vapors of specific classes of molecules. The resulting array, or "signature" identifies specific compounds.

The operating performance of most chemical sensors that use a chemoselective film coating is greatly affected by the thickness, uniformity and composition of the coating. For these sensors, increasing the coating thickness, has a detrimental effect on the sensitivity. Only the transducer senses the portion of the coating immediately adjacent to the transducer/substrate.

For example, if the polymer coating is too thick, the sensitivity of a SAW device to record changes in frequency will be reduced. These outer layers of coating material compete for the marker with the layers of coating being sensed and thus reduce the sensitivity of the sensor. Uniformity of the coating is also a critical factor in the performance of a sensor that uses a chemoselective coating since changes in average surface area greatly affect the local vibrational signature of the SAW device. Therefore, films should be deposited that are flat to within 1 nm with a thickness of 15-25 nm. In this regard, it is important not only that the coating be uniform and reproducible from one device to another, so that a set of devices will all operate with the same sensitivity, but also that the coating on a single device be uniform across the active area of the substrate.

If a coating is non-uniform, the response time to marker exposure and the recovery time after marker exposure are increased and the operating performance of the sensor is impaired. The thin areas of the coating respond more rapidly to a target marker than the thick areas. As a result, the sensor response signal takes longer to reach an equilibrium value, and the results are less accurate than they would be with a uniform coating.

Most current technologies for creating large area films of polymers and biomaterials involve the spinning, spraying, or dipping of a substrate into a solution of the macromolecule and a volatile solvent. These methods coat the entire substrate without selectivity and sometimes lead to solvent contamination and morphological inhomogeneities in the film due to non-uniform solvent evaporation. There are also techniques such as microcontact printing and hydrogel stamping that enable small areas of biomolecular and polymer monolayers to be patterned, but separate techniques like photolithography or chemical vapor deposition are needed to transform these films into microdevices.

Other techniques such as thermal evaporation and pulsed laser ablation are limited to polymers that are stable and not denatured by vigorous thermal processes. More precise and accurate control over the thickness and uniformity of a film coating may be achieved by using pulsed laser deposition (PLD), a physical vapor deposition technique that has been developed recently for forming ceramic coatings on substrates. By this method, a target comprising the stoichiometric chemical composition of the material to be used for the coating is ablated by means of a pulsed laser, forming a plume of ablated material that becomes deposited on the substrate.

Polymer thin films, using a new laser based technique developed by researchers at the Naval Research Laboratory called Matrix Assisted Pulsed Laser Evaporation (MAPLE), have recently been shown to increase sensitivity and specificity of chemoselective Surface Acoustic Wave vapor sensors. By providing improved SAW biosensor response by eliminating film imperfections induced by solvent evaporation and detecting molecular attachments to specific target markers, high sensitivity and specificity is possible.

Certain extremely sensitive, commercial off-the-shelf (COTS) electronic noses, such as those provided by Cyrano Sciences, Inc. ("CSI") (i.e., CSI's Portable Electronic Nose and CSI's Nose-Chip integrated circuit for odor-sensing, see U.S. Pat. No. 5,945,069—FIG. 1), may be used in the system and method of the present invention to monitor the exhaled breath from a patient. These devices offer minimal cycle time, can detect multiple markers, can work in almost any environment without special sample preparation or isolation conditions, and do not require advanced sensor design or cleansing between tests.

In other embodiments, competitive binding immunoassays can be used to test a bodily fluid sample for the presence of signaling agents. Immunoassay tests generally include an absorbent, fibrous strip having one or more reagents incorporated at specific zones on the strip. The bodily fluid sample is deposited on the strip and by capillary action the sample will migrate along the strip, entering specific reagent zones in which a chemical reaction may take place. At least one reagent is included which manifests a detectable response, for example a color change, in the presence of a minimal amount of a signaling agent of interest. Patents that describe immunoassay technology include the following: U.S. Pat. Nos. 5,262,333 and 5,573,955, both of which are incorporated herein by reference in their entirety.

In one embodiment, the device of the present invention may be designed so that patients can exhale via the mouth or nose directly onto a sensor of the invention, without needing a breath sampling apparatus. For example, a mouthpiece or nosepiece will be provided for interfacing a patient with the device to readily transmit the exhaled breath to the sensor (See, i.e., U.S. Pat. No. 5,042,501). In a related embodiment, wherein the sensor is connected to a neural network, the output from the neural network is similar when the same patient exhales directly into the device and when the exhaled gases are allowed to dry before the sensor samples them.

In another embodiment, a patient's breath sample can be captured in a container (vessel) for later analysis using a sensor of the subject invention (i.e., mass spectrometer).

The humidity in the exhaled gases represents a problem for certain electronic nose devices (albeit not SAW sensors) that only work with "dry" gases. When using such humidity sensitive devices, the present invention may adapt such electronic nose technology so that a patient can exhale directly into the device with a means to dehumidify the samples. This is accomplished by including a commercial dehumidifier or a heat moisture exchanger (HME), a device designed to prevent desiccation of the airway during ventilation with dry gases.

Alternatively, the patient may exhale through their nose, which is an anatomical, physiological dehumidifier to prevent dehydration during normal respiration. Alternatively, the sensor device can be fitted with a preconcentrator, which has some of the properties of a GC column. The gas sample is routed through the preconcentrator before being passed over the sensor array. By heating and volatilizing the gases, humidity is removed and the marker being measured can be separated from potential interferents.

The results from the sensor technology analysis of the bodily fluid samples are optionally provided to the user (or patient) via a reporting means. In one embodiment, the sensor technology includes the reporting means. Contemplated reporting means include a computer processor linked to the sensor technology in which electronic or printed results can be provided. Alternatively, the reporting means can include a digital display panel, transportable read/write magnetic media such as computer disks and tapes which can be transported to and read on another machine, and printers such as thermal, laser or ink-jet printers for the production of a printed report.

The reporting means can provide the results to the user (or patient) via facsimile, electronic mail, mail or courier service, or any other means of safely and securely sending the report to the patient. Interactive reporting means are also contemplated by the present invention, such as an interactive voice response system, interactive computer-based reporting system, interactive telephone touch-tone system, or other similar system. The report provided to the user (or patient) may take many forms, including a summary of analyses performed over a particular period of time or detailed information regarding a particular bodily fluid sample analysis. Results may also be used to populate a financial database for billing the patient, or for populating a laboratory database or a statistical database.

A data monitor/analyzer can compare a pattern of response to previously measured and characterized responses from known markers. The matching of those patterns can be performed using a number of techniques, including neural networks. By comparing the analog output from each of the 32 polymers to a "blank" or control, for example, a neural network can establish a pattern that is unique to that marker and subsequently learns to recognize that marker. The particular resistor geometries are selected to optimize the desired response to the target markerbeing sensed. The sensor of the subject invention is preferably a self-calibrating polymer system suitable for detecting and quantifying markers in gas phase biological solutions to assess and/or monitor a variety of therapeutic drug markers simultaneously.

According to the subject invention, the sensor can include a computer that communicates therewith, which can also notify the medical staff and/or the patient as to any irregularities in dosing, dangerous drug interactions, and the like. This system will enable determination as to whether a patient has been administered a pharmacologically effective amount of a therapeutic drug. The device could also alert the patient (or user) as to time intervals and/or dosage of therapeutic drug to be administered. Accordingly, it is contemplated herein that a sensor of the subject invention can be portable.

Preferably, in operation, the sensor will be used to identify a baseline spectrum for the patient prior to drug administration, if necessary. This will prove beneficial for the detection of more than one therapeutic drug if the patient receives more than one drug at a time and possible interference from different foods and odors in the stomach, mouth, esophagus and lungs.

Remote Communication System

A further embodiment of the invention includes a communications device in the home (or other remote location) that will be interfaced to the sensor. The home communications device will be able to transmit immediately or at prescribed intervals directly or over a standard telephone line (or other communication transmittal means) the data collected by the data monitor/analyzer device. The communication of the data will allow the user (i.e., physician) to be able to remotely verify if the appropriate dosage of a therapeutic drug is being administered to the patient. The data transmitted from the home can also be downloaded to a computer where the drug blood levels are stored in a database, and any deviations outside of pharmacological efficacy would be automatically flagged (i.e., alarm) so that a user (i.e., patient, physician, nurse) could appropriately adjust the drug dosage per suggestions provided by a computer processing unit connected to the sensor or per dosage suggestions provided by health care personnel (i.e., physician).

Endogenous Compounds

According to the present invention, the blood concentration of endogenous compounds can be monitored by utilizing breath sensor technology to detect and/or quantify endogenous compound markers present in exhaled breath. It has been shown that blood and exhaled concentration of certain therapeutic agents (such as propofol) are proportional. However, there has been no indication to date that endogenous compound markers are present in exhaled breath, let alone that the concentration of endogenous compounds in a human's body, specifically in patient blood, are proportional to those present in exhaled breath.

The present inventors have surprisingly discovered that endogenous compounds and/or their markers are present in exhaled breath and can be detected using the sensor technology described herein. In particular, endogenous compounds that are hydrophilic are likely to be measured in the liquid (exhaled breath condensate) phase of breath whereas those that are hydrophobic (lipophilic) are likely to be measured in the gas phase of breath. Further, the present inventors have discovered certain endogenous compounds, such as glucose, to be present in exhaled breath and that the concentration of the endogenous compounds in exhaled breath is proportional to the concentration in patient blood.

For example, a researcher ingested a 100 gm glucose solution and sampled breath and blood glucose levels 40 and 20 minutes before ingestion and multiple times for 120 minutes after ingestion. Glucose was readily detectable in the exhaled breath, which was condensed into a liquid. The concentration of both the breath and blood glucose rose and fell at the same rates. Correlation would be even tighter if only end-tidal breath samples were collected.

This and several other experiments suggest that the ratio of exhaled breath to blood glucose concentration is 1:10,000 and that this ratio is predictable and reproducible. In accordance with the present invention, a more predictive method is provided to monitor endogenous compound concentration in a patient by monitoring breath rather than blood. The systems and methods of the invention may be used to monitor such endogenous compounds as, but not limited to, glucose; proteins (e.g., heat shock proteins HSP70); urobilinogen; urobilirubin; bilirubin; hormones including cortisol, testosterone, estrogens, and pregnancy markers (e.g., hCG and its subunits); oligonucleotides (e.g., DNA, RNA); adenosine; adenosine triphosphate (ATP); adenosine diphosphate (ADP); adenosine monophosphate (AMP); prostaglandins (e.g., PGF2α); leukotrienes; cytokines; interleukins; melatonin; 6-sulfoxymelatonin; hypoxia-inducible factor 1α (HIF-1α); myogenic regulatory factors; 2,3-diphosphoglycerate (2,3-DPG); ketones; nitrite; electrolytes (e.g., sodium, chlorine, potassium, magnesium, calcium, bicarbonate, sulfates, phosphates); urea (blood urea nitrogen); uric acid; ammonia; lacetic acid; cholesterol; triglycerides (and other "fats" such as high density and low density lipoproteins); lactate dehydrogenase (LDH); cancer "markers" such as PSA (prostate specific antigen); and liver (SGOT, SGPT) and cardiac (and other muscle) enzymes: creatinine phosphokinase (CPK), troponin.

In view of the above, the present invention provides the capability of non-invasively, and in certain instances continuously, measuring a wide variety of endogenous compound concentrations in blood using exhaled breath as a surrogate, providing a physician with the ability to monitor and diagnose a variety of ailments, such as renal, hepatic, pancreatic, gastrointestinal, and cardiovascular problems via breath collection.

Where endogenous compound levels are continuously monitored, healthcare workers need only intervene if the sensor technology described herein indicates that a medical concern exists, which can be relayed in the form of an alarm system triggered if abnormal endogenous compound concentration levels exceed a predetermined limit over a given period of time. Electrical output signal(s) that can be produced by a sensor device of the invention can enable remote computer monitoring of endogenous compound concentrations in a patient to provide early indicators of ailments, which is especially important for diabetic and disabled patients and can greatly reduce the cost of long-term health care.

In one embodiment, a system of the invention comprises a sensor device, a computing/processor device, a system controller, and a controlled supply means for automated delivery of a therapeutic drug. The sensor device preferably detects endogenous compound marker concentration in breath and is connected to communicate the results to the computing/processor device.

The computing/processor device runs under control of a program stored in the memory of the computing/processor device and determines a desired therapeutic drug and/or dosage of a therapeutic drug in response to the results provided by the sensor. Preferably, the computing/processor device comprises a data monitor/analyzer that can compare a pattern of results communicated from the sensor device to previously measured and characterized results, where the results are indicative of patient condition. The computing/processor device preferably utilizes a trainable neural network to determine the therapeutic drug and/o therapeutic drug dosage to be administered to the patient based on the patient's condition and generates a response signal. In one embodiment, responsive to the response signal of the computing/processor device, the system controller directs the controlled supply means to dispense a dosage or adjust a dosage for a therapeutic drug.

In operation, upon detection of the target marker, the concentration of the endogenous compound in blood can be determined by the computing/processor device for use in establishing clinically relevant data regarding the patient's condition and, when appropriate, deriving the appropriate type of therapeutic drug and dosage amount to be delivered to the patient to address the patient's condition. In certain embodiments, such information regarding appropriate drug and dosage is communicated to the user.

In a preferred embodiment, an automated system is provided for monitoring the concentration of glucose present in breath, where the concentration of glucose is indicative of blood glucose concentration, which can be used to derive diabetic patient condition. Specifically, patient exhaled breath is applied to a sensor (such as an electronic nose), which continuously or intermittently communicates results to a computing/processor device to derive the concentration of glucose present in breath (and corresponding level of glucose in blood). Based on the monitored glucose concentration in breath, the computing/processor device communicates with the system controller of the invention, which will direct the controlled supply means (e.g., IV bag) to dispense (or refrain from dispensing) an appropriate dosage of a therapeutic drug, such as insulin, to address the patient's condition. For example, where the computing/processor device assesses that the glucose levels in the patient's blood are too high, the system of the invention can automatically deliver insulin to the patient to lower blood glucose levels.

Pharmacodynamics and Pharmacokinetics of Therapeutic Drugs

When a therapeutic drug is administered to a patient in accordance with the subject invention, there are many factors which effect drug pharmacodynamics and pharmacokinetics. For example, drug affinity (i.e., degree of attraction between a drug and a target receptor in the patient body), drug distribution (i.e., binding of drug to proteins circulating in the blood, absorption of drug into fat), drug metabolism and elimination (i.e., renal clearance), or existence of a drug in a "free" form may affect drug pharmacodynamics and pharmacokinetics (PD/PK) in a patient.

A drug bound to protein or absorbed into fat does not produce a desired pharmacological effect and exists in equilibrium with unbound drug. Numerous factors, including competition for binding sites on the protein from other drugs, the amount of fat in the body, and the amount of protein produced, determine the equilibrium between bound and unbound drug.

An unbound drug can participate directly in the pharmacological effect or be metabolized into a drug that produces a desired effect. Metabolism of the active drug often leads to its removal from the bloodstream and termination of its effect. The drug effect can also be terminated by the excretion of the free drug. Free drug or a metabolite can be excreted in the urine or the digestive tract or in exhaled breath. The concentration in the blood (or plasma or serum) of such therapeutic drugs is related to the clinical effect of the agent.

As described above, blood concentration testing for a therapeutic drug may or may not provide an accurate indication of the effect of the therapeutic drug on a patient, since measurement of blood concentration does not account for the quantity of drug bound to protein or membranes, or the interaction and competition between drugs. For this reason, it would be advantageous to measure only the free drug in the plasma. The concentration of free drug in plasma is usually low and requires sophisticated and expensive analytical techniques for measurement. By contrast, the marker that appears in breath, in accordance with the subject invention, is an indication of the concentration of free drug in blood. Thus, using the systems and methods of the subject invention to measure exhaled breath for marker concentration can provide an effective indicator of the actual concentration of free drug responsible for PK effect.

Further, testing blood directly (i.e., drawing blood for sample analysis) is invasive, time consuming, expensive, and prone to inaccuracies. In contrast, by analyzing therapeutic drug markers in patient exhaled breath, the systems and methods of the subject invention are non-invasive, speedy, and accurate and can be performed intermittently or continuously. When a therapeutic drug marker (such as the therapeutic drug or its metabolite) is excreted in the breath, the concentration in expired breath is proportional to the free therapeutic drug (or metabolite) concentration in the blood and, thus, indicative of the rate of drug absorption, distribution, metabolism, and/or elimination.

In certain embodiments, the metabolite measured in exhaled breath may be the active metabolite or a breakdown product of the active therapeutic drug. As long as there is equilibrium between the active drug and a metabolite (such as an inactive metabolite) excreted in the breath, the activity of the active drug can be analyzed in accordance with the subject invention.

The method of the present invention takes into account such proportional concentrations and allows for the determination of the rate of absorption, distribution, metabolism, and elimination of a therapeutic drug by measuring concentration of unbound substances, markers, and/or active metabolites associated with the drug in a patient's breath. The proper dosing regimen can thus be determined therefrom.

Therapeutic Drug Markers

In accordance with the present invention, therapeutic drug markers useful as an indication of therapeutic drug concentration in blood include the following olfactory markers, without limitation: dimethyl sulfoxide (DMSO), acetaldehyde, acetophenone, trans-Anethole (1-methoxy-4-propenyl benzene) (anise), benzaldehyde (benzoic aldehyde), benzyl alcohol, benzyl cinnamate, cadinene, camphene, camphor, cinnamaldehyde (3-phenylpropenal), garlic, citronellal, cresol, cyclohexane, eucalyptol, and eugenol, eugenyl methyl ether; butyl isobutyrate (n-butyl 2, methyl propanoate) (pineapple); citral (2-trans-3,7-dimethyl-2,6-actadiene-1-al); menthol (1-methyl-4-isopropylcyclohexane-3-ol); and α-Pinene (2,6,6-trimethylbicyclo-(3,1,1)-2-heptene). These markers are preferred since they are used in the food industry as flavor ingredients and are permitted by the Food and Drug Administration. As indicated above, olfactory markers for use in the present invention can be selected from a vast number of available compounds (see *Fenaroli's Handbook of Flavor Ingredients*, 4$^{th}$ edition, CRC Press, 2001) and use of such other applicable markers is contemplated herein.

The markers of the invention also include additives that have been federally approved and categorized as GRAS ("generally recognized as safe"), which are available on a database maintained by the U.S. Food and Drug Administration Center for Food Safety and Applied Nutrition. Markers categorized as GRAS that are readily detectable in exhaled breath include, but are not limited to, sodium bisulfate, dioctyl sodium sulfosuccinate, polyglycerol polyricinoleic acid, calcium casein peptone-calcium phosphate, botanicals (i.e., chrysanthemum; licorice; jellywort, honeysuckle; lophatherum, mulberry leaf; frangipani; selfheal; sophora flower bud), ferrous bisglycinate chelate, seaweed-derived calcium, DHASCO (docosahexaenoic acid-rich single-cell oil) and ARASCO (arachidonic acid-rich single-cell oil), fructooligosaccharide, trehalose, gamma cyclodextrin, phytosterol esters, gum arabic, potassium bisulfate, stearyl alcohol, erythritol, D-tagatose, and mycoprotein.

Halogenated compounds (i.e. fluorinated drugs or markers) hold particular promise as they are readily highly volatile, safe for human consumption, and are readily detected in exhaled breath with portable Freon leak detectors. Some of these compounds are used as propellants for delivery of drugs via the pulmonary route, such as metered dose inhalers and therefore are known to be safe and are FDA approved, some are GRAS compounds as well. The technologies most often used to detect Freon leaks include: Negative Ion Capture, Heated Sensor/Ceramic Semiconductor, Infrared Absorption, and TIF TIFXP-1A Negative Corona Leak Detector. Many drugs are fluorinated and metabolites are often extremely volatile and detectable in exhaled breath. Numerous such compounds are available that could be used as markers and could be added as excipients during the manufacture of drugs.

As described above, therapeutic drug markers are detected by their physical and/or chemical properties, which does not preclude using the desired therapeutic drug itself as its own marker. Therapeutic drug markers, as contemplated herein, also include products and compounds that are administered to enhance detection using sensors of the invention. Moreover, therapeutic drug markers can include a variety of products or compounds that are added to a desired therapeutic drug regimen to enhance differentiation in detection/quantification. Generally, in accordance with the present invention, therapeutic drug markers are poorly soluble in water, which enhances their volatility and detection in the breath.

According to the subject invention, upon administering a therapeutic drug (wherein the therapeutic drug is the marker) or upon concurrent administration of a therapeutic drug and a detectable additive, the detection of the marker (such as the therapeutic drug, a metabolite of the therapeutic drug, or additive) can occur under several circumstances. In one example where the drug is administered orally, the marker can "coat" or persist in the mouth, esophagus and/or stomach upon ingestion and be detected with exhalation (similar to the taste or flavor that remains in the mouth after eating a breath mint).

In a second instance where the drug (and, when present, detectable additive) is administered orally, the drug may react in the mouth or stomach with acid or enzymes to produce or liberate the marker that can then be detected upon exhalation. Thirdly, the drug and/or marker can be absorbed in the gastrointestinal tract and be excreted in the lungs (i.e. alcohol is rapidly absorbed and detected with a Breathalyzer). Generally, a therapeutic drug marker of the invention provides a means for determining the pharmacodynamics and pharmacokinetics of the drug.

In one embodiment, a detectable additive (marker) is concurrently administered with a therapeutic drug (i.e., detectable additive is provided in a pharmaceutically acceptable carrier, detectable additive is provided in medication coating composed of rapidly dissolving glucose and/or sucrose). In a preferred embodiment, the therapeutic drug is provided in the form of a pill, whose coating includes at least one marker in air-flocculated sugar crystals. This would stimulate salivation and serve to spread the marker around the oral cavity, enhancing the lifetime in the cavity. Since the throat and esophagus could also be coated with the marker as the medication is ingested, detection of the marker is further enhanced.

Thus, when a drug is administered to a patient, the preferred embodiment of the invention detects and quantifies a therapeutic drug marker almost immediately in the exhaled breath of the patient (or possibly by requesting the patient to deliberately produce a burp) using a sensor (i.e., electronic nose). Certain drug compositions might not be detectable in the exhaled breath. Others might have a coating to prevent the medication from dissolving in the stomach. In both instances, as an alternate embodiment, a non-toxic olfactory marker (i.e., volatile organic vapors) can be added to the pharmaceutically acceptable carrier (i.e., the coating of a pill, in a separate fast dissolving compartment in the pill, or solution, if the drug is administered in liquid or suspension form) to provide a means for identifying/quantifying the marker in exhaled breath and thus determine the drug concentration in blood.

Preferably the marker will coat the oral cavity or esophagus or stomach for a short while and be exhaled in the breath (or in a burp). For drugs administered in the form of pills, capsules, and fast-dissolving tablets, the markers can be applied as coatings or physically combined or added to therapeutic drug. Markers can also be included with therapeutic drugs that are administered in liquid form (i.e., syrups, via inhalers, or other dosing means).

The therapeutic drug markers of the invention could be used for indicating specific drugs or for a class of drugs. For example, a patient may be taking an anti-depressant (tricyclics such as nortriptyline), antibiotic, an antihypertensive agent (i.e., clonidine), pain medication, and an anti-reflux drug. One marker could be used for antibiotics as a class, or for subclasses of antibiotics, such as erythromycins. Another marker could be used for antihypertensives as a class, or for specific subclasses of antihypertensives, such as calcium channel blockers. The same would be true for the anti-reflux drug. Furthermore, combinations of marker substances could be used allowing a rather small number of markers to specifically identify a large number of medications.

Therapeutic Drugs

As contemplated herein, therapeutic drugs to be monitored in accordance with the subject invention include, but are not limited to, anesthetic agents, psychiatric drugs (i.e., antidepressants, anti-psychotics, anti-anxiety drugs, depressants), analgesics, stimulants, biological response modifiers, NSAIDs, corticosteroids, disease-modifying antirheumatic drugs (DMARDs), anabolic steroids, antacids, antiarrhythmics, antibacterials, antibiotics, anticoagulants and thrombolytics, anticonvulsants, antidiarrheals, antiemetics, antihistamines, antihypertensives, anti-inflammatories, antineoplastics, antipyretics, antivirals, barbiturates, P-blockers, bronchodilators, cough suppressants, cytotoxics, decongestants, diuretics, expectorants, hormones, immunosuppressives, hypoglycemics, laxatives, muscle relaxants, sedatives, tranquilizers, and vitamins.

For example, the subject invention can effectively monitor concentrations of the following non-limiting list of therapeutic drugs in blood: drugs for the treatment of rheumatoid arthritis or symptoms thereof, systemic lupus erythematosus or symptoms thereof, degenerative arthritis, vasculitis, inflammatory diseases, angina, coronary artery disease, peripheral vascular disease; ulcerative colitis, and Crohn's disease; anti organ rejection drugs; antiepilepsy medication; and anti-anxiety drugs.

Therapeutic drugs whose concentration levels in blood can be monitored in accordance with the subject invention include, but are not limited to, the following: α-Hydroxy-Alprazolam; Acecamide (NAPA); Acetaminophen (Tylenol); Acetylmorphine; Acetylsalicylic Acid (as Salicylates); α-hydroxy-alprazolam; Alprazolam (Xanax); Amantadine (Symmetrel); Ambien (Zolpidem); Amikacin (Amikin); Amiodarone (Cordarone); Amitriptyline (Elavil) & Nortriptyline; Amobarbital (Amytal); Anafranil (Clomipramine) & Desmethyldlomipramine; Ativan (Lorazepam); Aventyl (Nortriptyline); Benadryl (Dephenhydramine); Benziodiazepines; Benzoylecgonine; Benztropine (Cogentin); Bupivacaine (Marcaine); Bupropion (Wellbutrin) and Hydroxybupropion; Butabarbital (Butisol); Butalbital (Fiorinal) Carbamazepine (Tegretol); Cardizem (Diltiazem); Carisoprodol (Soma) & Meprobamate; and Celexa (Citalopram & Desmethylcitalopram).

Additional therapeutic drugs whose blood concentration levels can be monitored in accordance with the subject invention include Celontin (Methsuximide) (as desmethylmethsuximide); Centrax (Prazepam) (as Desmethyldiazepam); Chloramphenicol (Chloromycetin); Chlordiazepoxide; Chlorpromazine (Thorazine); Chlorpropamide (Diabinese); Clonazepam (Klonopin); Clorazepate (Tranxene); Clozapine; Cocaethylene; Codeine; Cogentin (Benztropine); Compazine (Prochlorperazine); Cordarone (Amiodarone); Coumadin (Warfarin); Cyclobenzaprine (Flexeril); Cyclosporine (Sandimmwue); Cylert (Pemoline); Dalmane (Flurazepam) & Desalkylflurazepam; Darvocet; Darvon (Propoxyphene) & Norpropoxyphene; Demerol (Meperidine) & Normeperidine; Depakene (Valproic Acid); Depakote (Divalproex) (Measured as Valproic Acid); Desipramine (Norpramin); Desmethyldiazepaam; Desyrel (Trazodone); Diazepam & Desmethyldiazepam; Diazepam (Valium) Desmethyldiazepam; Dieldrin; Digoxin (Lanoxin); Dilantin (Phenyloin); Disopyramide (Norpace); Dolophine (Methadone); Doriden (Glutethimide); Doxepin (Sinequan) and Desmethyldoxepin; Effexor (Venlafaxine); Ephedrine; Equallil (Meprobamate) Ethanol; Ethosuximide (Zarontin); Ethotoin (Peganone); Felbamate (Felbatol); Fentanyl (Innovar); Fioricet; Fipronil; Flunitrazepam (Rohypnol); Fluoxetine (Prozac) & Norfluoxetine; Fluphenazine (Prolixin); Fluvoxamine (Luvox); Gabapentin (Neurontin); Gamma-Hydroxybutyric Acid (GHB); Garamycin (Gentamicin); Gentamicin (Garamycin); Halazepam (Paxipam); Halcion (Triazolam); Haldol (Haloperidol); Hydrocodone (Hycodan); Hydroxyzine (Vistaril); Ibuprofen (Advil, Motrin, Nuprin, Rufen); imipramine (Tofranil) and Desipramine; Inderal (Propranolol); Keppra (Levetiracetam); Ketamine; Lamotrigine (Lamictal); Lanoxin (Digoxin); Lidocaine (Xylocalne); Lindane (Gamma-BHC); Lithium; Lopressor (Metoprolol); Lorazepam (Ativan); and Ludiomil.

Blood level concentrations of the following therapeutic drugs that can be monitored in accordance with the subject invention include, but are not limited to, Maprotiline; Mebaral (Mephobarbital) & Phenobarbital; Mellaril (Thioridazine) & Mesoridazine; Mephenyloin (Mesantoin); Meprobamate (Miltown, Equanil); Mesantoin (Mephenyloin); Mesoridazine (Serentil); Methadone; Methotrexate (Mexate); Methsuximide (Celontin) (as desmethsuximide); Mexiletine (Mexitil); Midazolam (Versed); Mirtazapine (Remeron); Mogadone (Nitrazepam); Molindone (Moban); Morphine; Mysoline (Primidone) & Phenobarbital; NAPA & Procainamide (Pronestyl); NAPA (N-Acetyl-Procainamide); Navane (Thiothixene); Nebcin (Tobramycin); Nefazodone (Serzone); Nembutal (Pentobarbital); Nordiazepam; Olanzapine (Zyprexa); Opiates; Orinase (Tolbutamide); Oxazepnam (Serax); Oxcarbazepine (Trileptal) as 10-Hydroxyoxcarbazepine; Oxycodone (Percodan); Oxymorphone (Numorphan); Pamelor (Nortriptyline); Paroxetine (Paxil); Paxil (Paroxetine); Paxipam (Halazepam); Peganone (Ethotoin); PEMA (Phenylethylmalonamide); Pentothal (Thiopental); Perphenazine (Trilafon); Phenergan (Promethazine); Phenothiazine; Phentermine; Phenylglyoxylic Acid; Procainamide (Pronestyl) & NAPA; Promazine (Sparine); Propafenone (Rythmol); Protriptyline (Vivactyl); Pseudoephedrine; Quetiapine (Seroquel); Restoril (Temazepam); Risperdal (Risperidone) and Hydroxyrisperidone; Secobarbital (Seconal); Sertraline (Zoloft) & Desmethylsertraline; Stelazine (Trifluoperazine); Surmontil (Trimipramine); Tocamide (Tonocard); and Topamax (Topiramate).

Therapeutic drugs of the subject invention can be formulated according to known methods for preparing pharmaceutically useful compositions. Formulations are described in a number of sources, which are well known and readily available to those skilled in the art. For example, *Remington's Pharmaceutical Science* (Martin E W [1995] Easton Pa., Mack Publishing Company, $19^{th}$ ed.) describes formulations that can be used in connection with the subject invention. Formulations suitable for parenteral administration include, for example, aqueous sterile injection solutions, which may contain antioxidants, buffers, bacteriostats, and solutes, which render the formulation isotonic with the blood of the intended recipient; and aqueous and nonaqueous sterile suspensions, which may include suspending agents and thickening agents.

Formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question.

Administration of a therapeutic drug, in accordance with the subject invention, can be accomplished by any suitable method and technique presently or prospectively known to those skilled in the art. In a preferred embodiment, a therapeutic drug is formulated in a patentable and easily consumed oral formulation such as a pill, lozenge, tablet, gum, beverage, etc.

According to the subject invention, a therapeutic drug can be delivered from a controlled supply means (i.e., pill dispenser, IV bag, etc.). Upon delivery of the therapeutic drug to a patient, a sensor of the invention analyzes a patient's expired gases to detect at least one target marker of the therapeutic drug. Upon detection of the target marker, the concentration of the therapeutic drug in blood can be determined for use in deriving the appropriate dosage amount of the therapeutic drug to next be delivered to the patient. In one embodiment, a system controller utilizes the derived appropriate dosage based on exhaled breath analysis to dispense an appropriate dosage from the supply means to the patient.

Additional embodiments are also envisioned herein. Pulmonary delivery of medications is well known, especially for conditions such as asthma and chronic obstructive pulmonary disease. In these instances, medication (i.e. corticosteroids, bronchodilators, anticholinergics, etc.) is often nebulized or aerosolized and inhaled through the mouth directly into the lungs. This allows delivery directly to the affected organ (the lungs) and reduces side effects common with enteral (oral)

delivery. Metered dose inhalers (MDIs) or nebulizers are commonly used to deliver medication by this route. Recently dry powder inhalers have become increasingly popular, as they do not require the use of propellants such as CFCs. Propellants have been implicated in worsening asthma attacks, as well as depleting the ozone layer. Dry power inhalers are also being used for drugs that were previously given only by other routes, such as insulin, peptides, and hormones.

Olfactory markers can be added to these delivery systems as well. Since the devices are designed to deliver medication by the pulmonary route, the sensor array can be incorporated into the device and the patient need only exhale back through the device for documentation to occur.

Lastly, devices are available to deliver medication by the intranasal route. This route is often used for patients with viral infections or allergic rhinitis, but is being increasing used to deliver peptides and hormones as well. Again, it would be simple to incorporate a sensor array into these devices, or the patient can exhale through the nose for detection by a marker sensing system.

Following are examples which illustrate procedures for practicing the invention. These examples should not be construed as limiting. All percentages are by weight and all solvent mixture proportions are by volume unless otherwise noted.

EXAMPLE 1

Intravenous IV Anesthesia Delivery

During intravenous anesthesia, anesthetic agents are administered directly into a patient's bloodstream rather than administering gases through a breathing circuit. The administered drug may bind to proteins circulating in the blood, be absorbed into fat or exist in a "free" form. Drug bound to protein or absorbed in fat does not produce a pharmacological effect and exists in equilibrium with unbound drug. Numerous factors, including competition for binding sites on the protein from other drugs, the amount of fat in the body and the amount of protein produced, determine the equilibrium between bound and unbound drug. Unbound drug may participate directly in the pharmacological effect or be metabolized into a drug that produces the effect. Metabolism of the active drug often leads to its removal from the bloodstream and termination of its effect. The drug effect can also be terminated by the excretion of the free drug. Free drug or a metabolite can be excreted in the urine or the digestive tract or in exhaled breath. The concentration in the blood (or plasma or serum) of such agents (e.g., propofol, alfentanil and remifentanil) is related to the clinical effect of the agent.

Figure 3:
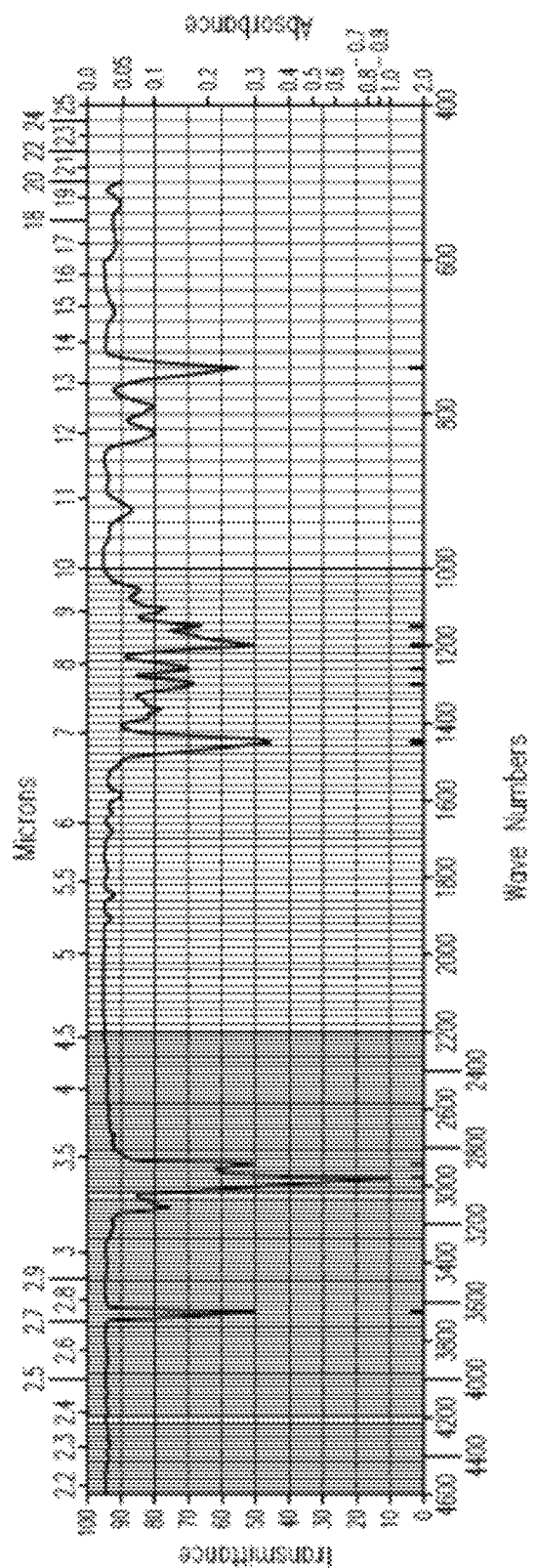
FIG. 3 shows the FT-IR signal for propofol.

FIG. 3 represents the FT-IR signal for propofol (2,6-diisopropylphenol). It has been specifically shown that there is a good correlation between blood concentration of anesthetic agents (e.g., propofol) and depth of anesthesia. Therefore, testing blood concentration is a good indicator of the effect of the agent (depth of anesthesia). Unfortunately, testing blood directly is invasive and time consuming. When a drug or its metabolite is excreted in the breath, the concentration in expired breath is proportional to the free drug or metabolite concentration in the blood and, thus, indicative of depth of anesthesia and/or the rate of drug metabolism. The metabolite measured in exhaled breath may be the active metabolite or a breakdown product of the active drug. As long as there is equilibrium between the active drug and an inactive metabolite excreted in the breath, the activity of the active drug will be known. The method of the present invention takes into account such proportional concentrations and allows for the determination of depth of anesthesia and/or the rate of metabolism of the drug by measuring concentration of unbound substances, agents and/or active metabolites in a patient's breath, see FIG. 4. The proper dosing regimen can thus be determined therefrom.

Generally, the exhalation gas stream comprises sequences or stages. At the beginning of exhalation there is an initial stage, the gas representative thereof coming from an anatomically inactive (deadspace) part of the respiratory system, in other words, from the mouth and upper respiratory tracts. This is followed by a plateau stage. Early in the plateau stage, the gas is a mixture of deadspace and metabolically active gases. The last portion of the exhaled breath comprises nothing but deep lung, so-called alveolar gas. This gas, which comes from the alveoli, is termed end-tidal gas. In one embodiment, the exhaled breath sample is collected at end-tidal breathing. Technology similar to that used for end-tidal carbon dioxide monitoring can be used to determine when the sample is collected. Airway pressure measurements afford another means of collecting samples at the appropriate phase of the respiratory cycle. Single or multiple samples collected by the side stream method are preferable, but if sensor acquisition time is reduced, in-line sampling may be used. In the former, samples are collected through an adapter at the proximal end of the endotracheal tube and drawn through thin bore tubing to the sensor chamber. Depending on the sample size and detector response time, gas may be collected on successive cycles. With in-line sampling, the sensor is placed proximal to the ET tube directly in the gas stream. Alternatively to sampling end-tidal gas, samples can be taken throughout the exhalation phase of respiration and average value determined and correlated with blood concentration.

Figure 5A:
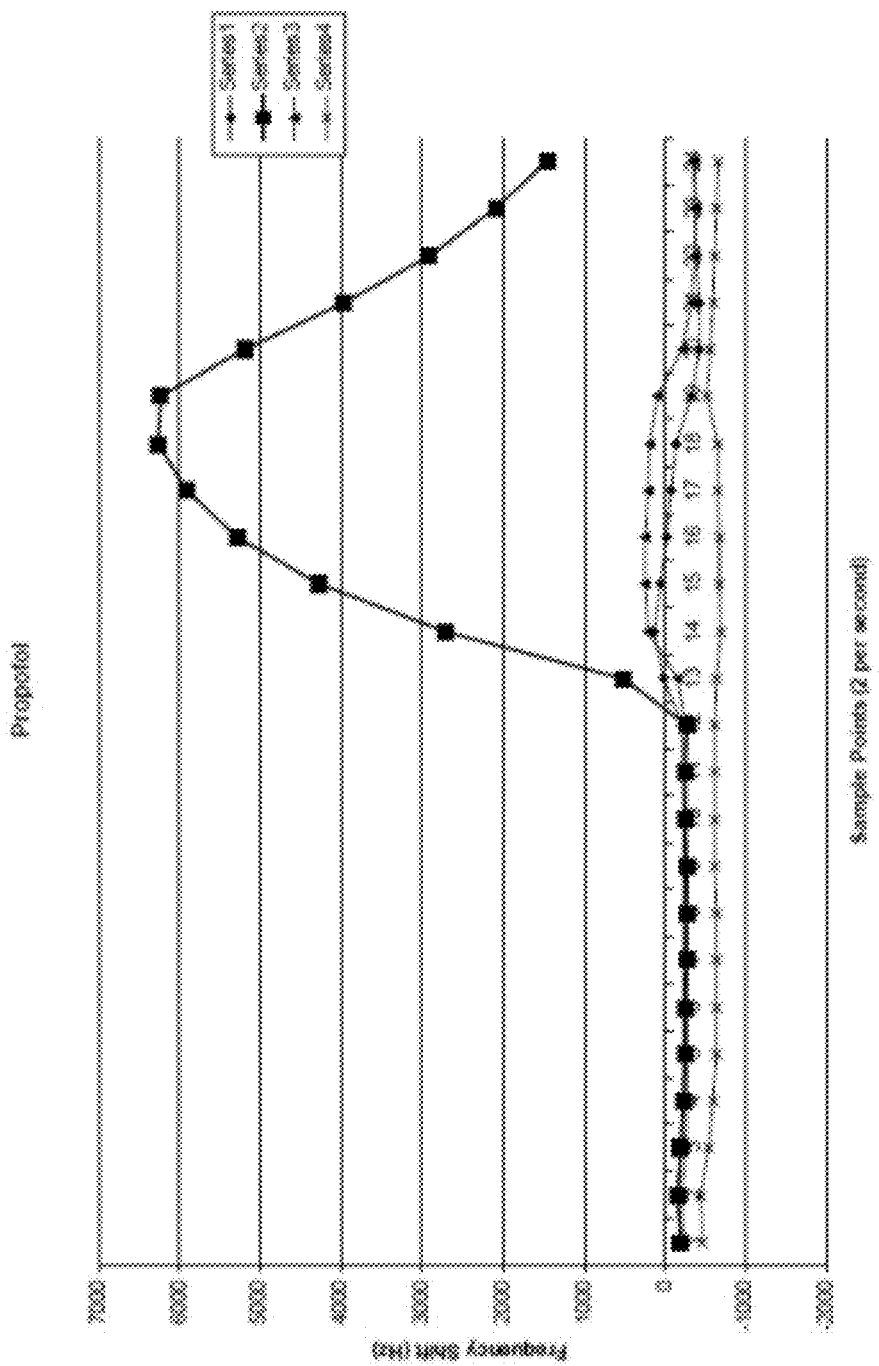
FIG. 5a shows the characteristic signature of propofol.

Referring now to FIG. 5a, the characteristic signature of propofol from a four (4) sensor polymer coated SAW array is shown. In this example, 1 cc of propofol was placed in a "headspace" gas chromatography vial. A 19-gauge hypodermic needle attached to a VaporLab™ gas detector containing the sensor array was inserted into the vial, which was heated to 37° C., and the "signature" was recorded. The VaporLab™ brand instrument is a hand-held, battery powered SAW based chemical vapor identification instrument suitable for detecting vapors in accordance with the present invention. This instrument is sensitive to volatile and semi-volatile compounds and has a high-stability SAW sensor array that provides orthogonal vapor responses for greater accuracy and discrimination. The device communicates with computers to provide enhanced pattern analysis and report generation. The device can be easily "trained" to remember chemical vapor signature patterns for fast, "on-the-fly" analysis. Note that the "signature" has both amplitude and temporal resolution. In the present invention, vapor concentration measurements of vapors are made by detecting the adsorption of molecules onto the surface of a SAW sensor coated with a polymer thin film. This thin film is specifically coated to provide selectivity and sensitivity to specific vapors. The SAW is inserted as an active feedback element in an oscillator circuit. A frequency counter measures the oscillation frequency, which corresponds to the resonant frequency of the SAW sensor. The response of the SAW sensor to the vapor is measured as a shift in the resonant frequency of the SAW sensor. This configuration requires an oscillator circuit, the coated SAW sensor, and a frequency counter, all of which can be housed on a small printed circuit board.

Figure 5B:
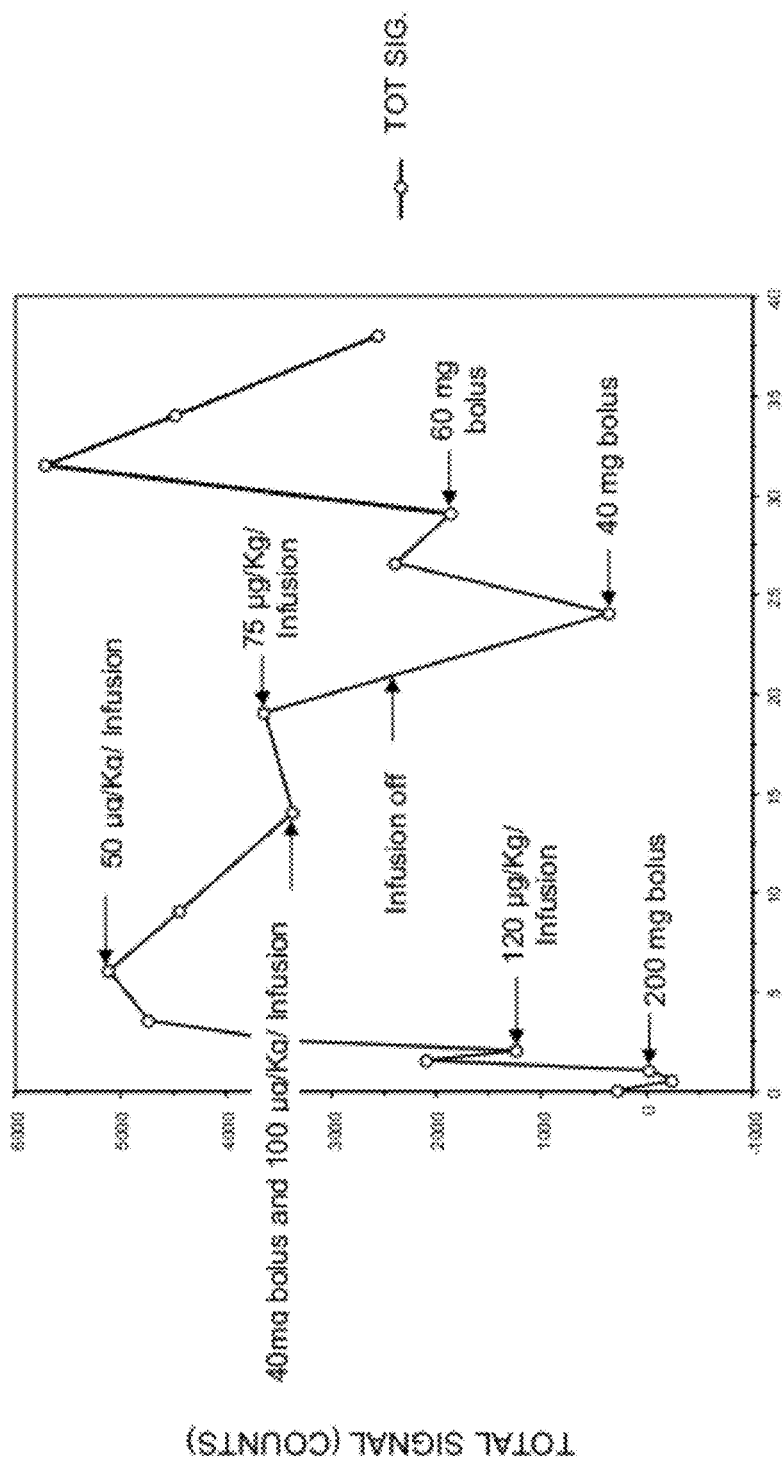
FIG. 5b shows a propofol relative breath concentration profile of a patient.

FIG. 5b shows an example of a Propofol relative breath concentration profile in a patient.

In another embodiment, samples are collected at the distal end of the endotracheal tube (ETT) through a tube with a separate sampling port. This may improve sampling by allowing a larger sample during each respiratory cycle.

The concentration of an anesthetic agent in the body is regulated both by the amount of the agent administered over a given time period and the rate at which the agent is eliminated from the body (metabolism). The present invention provides the steps of administering an agent to the subject and analyzing exhaled breath of the subject for concentration of unbound substances, active metabolites, or inactive metabolites after a suitable time period; the concentration indicates a characteristic of metabolism of the agent in the subject. The method may further include using a flow sensor to detect starting and completion of exhalation. The method further includes providing results from the analysis and controlling the infusion pump for delivering the intravenous anesthesia agent based on the results. Moreover, a CPU may be provided as a data processing/control unit for automatically detecting the signal from the flow sensor to control sampling of exhaled breath. The CPU may further provide the analysis and control of the infusion pump or other administering means.

Methods for administering the agent are readily understood by those skilled in the art. For example, an infusion pump may be used. Compounds may be also administered parenterally, sublingually, transdermally, by i.v. bolus, and by continuous infusion. A number of suitable agents are available for administration as also known by those skilled in the art (Remifentanil—Glaxo Wellcome, Propofol—Zeneca). Agents may also be those of amnesia, analgesia, muscle relaxation, and sedation agents or a combination thereof. Agents may be administered in an amount for analgesia, conscious sedation, or unconsciousness as known in the art. Patient characteristics may also be monitored during administration of the agent.

Concentration in the blood as measured by the breath analysis of the present invention for free agents or metabolites may indicate when the patient is receiving an anesthetic concentration (a high dose), an analgesic concentration (a low dose), or emerging from anesthesia as a result of a level that allows for full recovery. Even if there is wide variation in the metabolism or response to an anesthetic agent, knowledge of the exhaled breath concentration allows the anesthesiologist to know if the drug is accumulating in the blood, possibly leading to a dangerously deep level of anesthesia and/or a prolonged recovery time: or, the concentration is falling, possibly leading to inadequate anesthesia and premature emergence. Monitoring changes in concentration are, therefore, useful.

In another embodiment, the exhalation air is measured for free agent and/or metabolite concentration either continuously or periodically. From the exhalation air is extracted at least one measured free agent or metabolite concentration value. Numerous types of apparatus may be used to carry out the method of the present invention. In one embodiment, the apparatus includes a conventional flow channel through which exhalation air flows. The flow channel is provided with sensor elements for measuring free agent or metabolite concentration. Furthermore, the apparatus includes necessary output elements for delivering at least a measured concentration result to the operator, if necessary. An alarm mechanism may also be provided. An instrument of similar type is shown in FIGS. 1 and 2 of U.S. Pat. No. 5,971,937 incorporated herein by reference.

Figure 4:
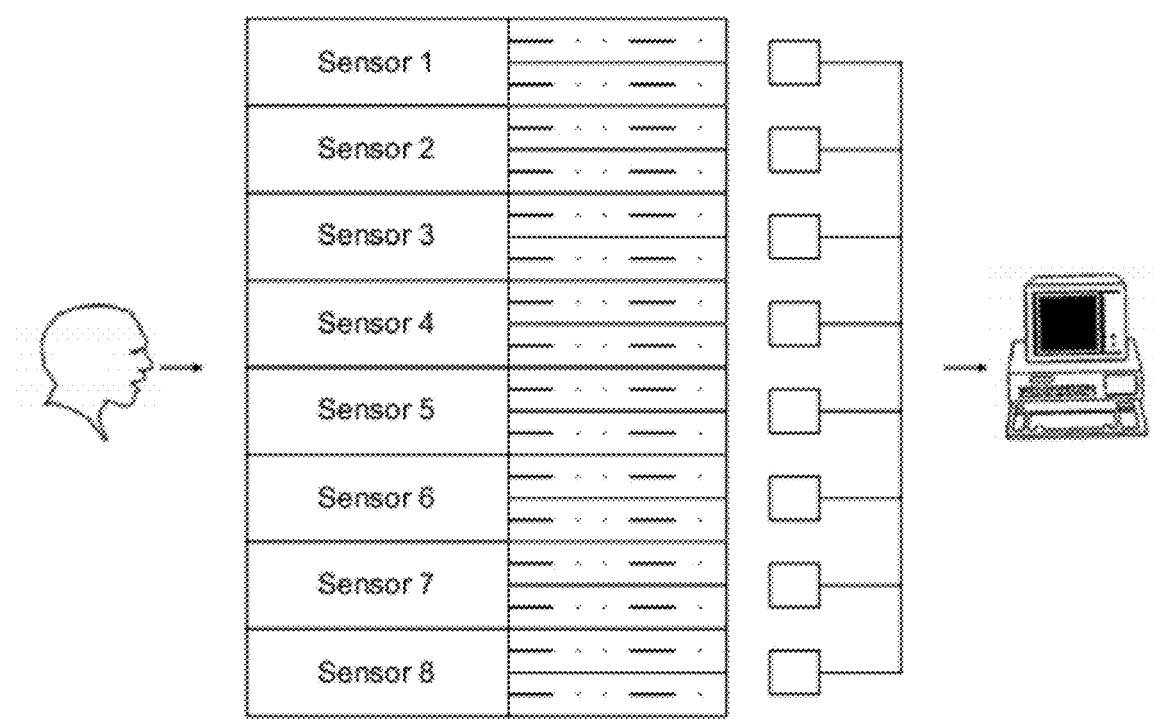
FIG. 4 shows an example of measuring expired breath of a patient utilizing a sensor.

In one embodiment, the device of the present invention may be designed so that patients can exhale via the mouth or nose directly into the device, FIG. 4.

Preferably, in operation, the sensor will be used to identify a baseline spectrum for the patient prior to delivery, if necessary. This will prove beneficial for the detection of more than one drug if the patient receives more than one drug at a time and possible interference from different foods and odors in the stomach, mouth, esophagus and lungs.

EXAMPLE 2

Inhalational Anesthesia

Inhalation agents are generally administered through a breathing system. A breathing system is an assembly of components which connects the patient's airway to the anesthetic machine, from and into which the patient breathes. As known in the art, such systems generally include a fresh gas entry port/delivery tube through which the gases are delivered from the machine; a port to connect it to the patient's airway (oral airway, mask, endotracheal tube); a reservoir for gas; a expiratory port/valve through which the expired gas is vented to the atmosphere; a carbon dioxide absorber (for rebreathing); and tubes for connecting these components. Flow directing valves may or may not be used.

Figure 6A:
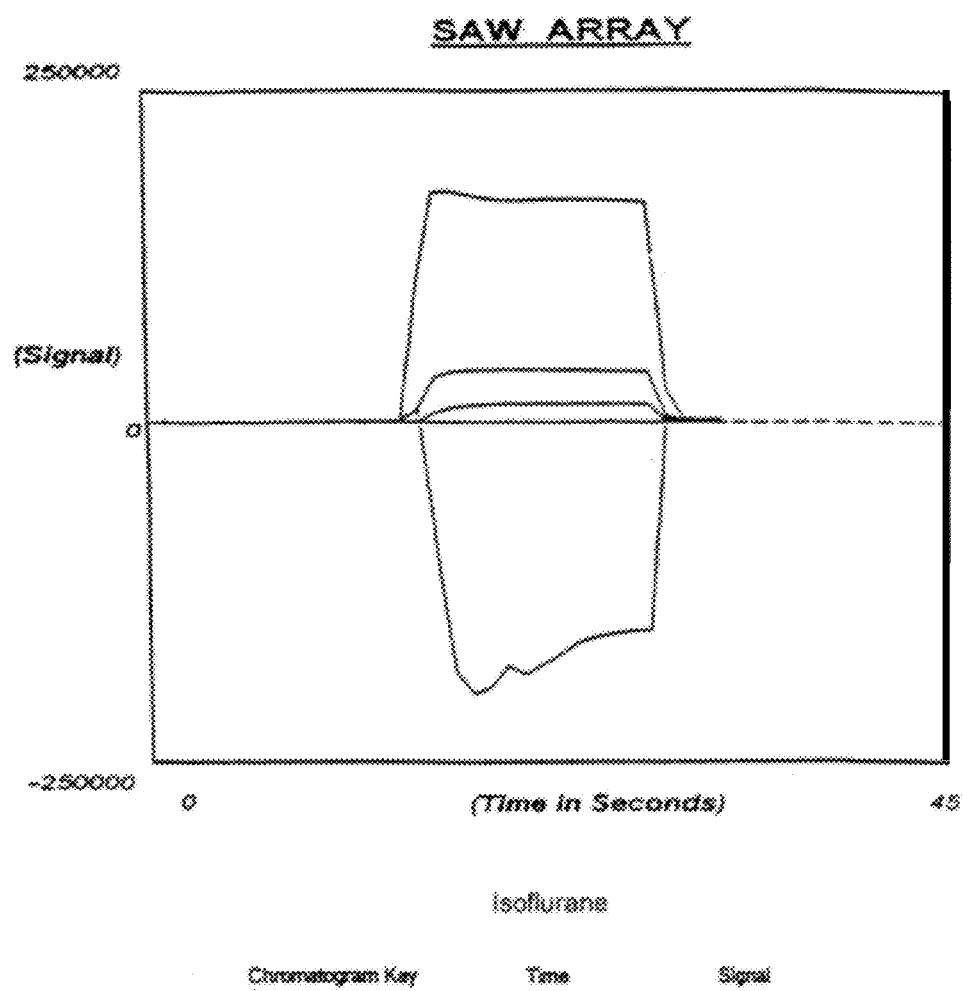
FIG. 6a shows the unique signature of Isoflurane derived from a SAW sensor.
Figure 6B:
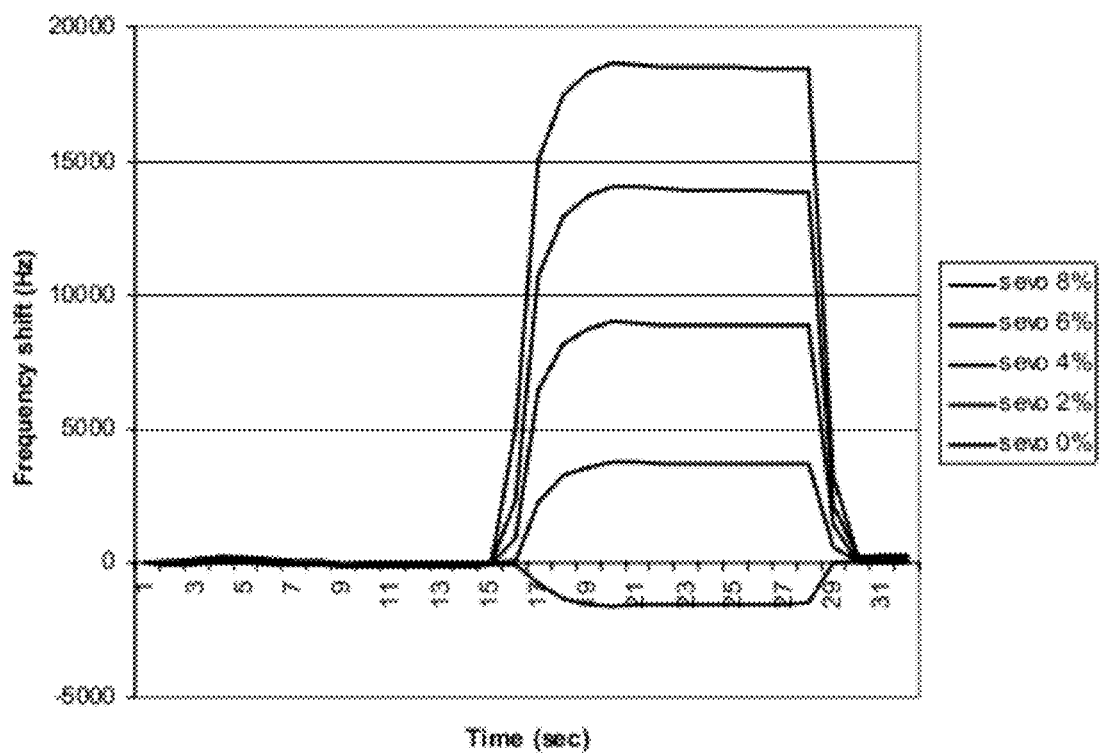
FIG. 6b shows the unique signature of Sevoflurane derived from a SAW sensor.
Figure 7A:
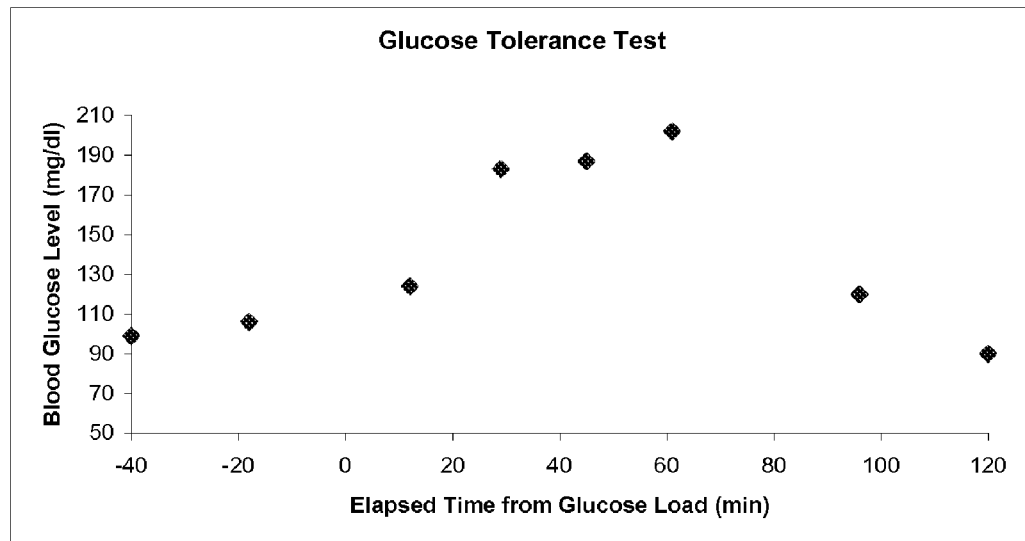
FIGS. 7a and 7b illustrate the blood (8a) and breath (8b) concentrations of glucose over time after the ingestion of a 100 gm glucose solution.
Figure 7B:
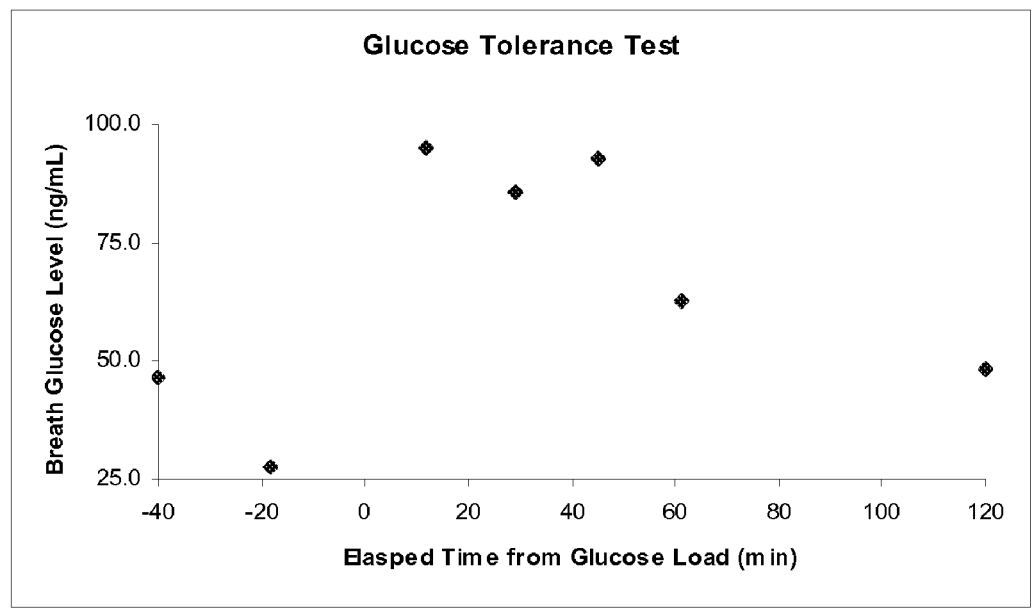

The sensors of the present invention are in communication with the delivered (inspired) gas and/or the expired gas of the breathing circuit to appropriately monitor the target substance(s). Preferably, the sensors are in flow communication with the appropriate tubes, valves, etc. of the circuit. FIGS. 6a and 6b show the unique signatures of the inhalational anesthetics Isoflurane and Sevoflurane, respectively, sampled from a breathing circuit. Sensors may be placed throughout the breathing circuit to obtain readings for target substances. Inspired gases are monitored by connecting the sensor(s) of the present invention to the appropriate location(s) in the breathing circuit. Similarly, expired gases are monitored by connecting the sensor(s) of the present invention to the appropriate location(s) in the breathing circuit. In an embodiment, samples are collected at the distal end of the endotracheal tube (ETT) through a tube with a separate sampling port. This may improve sampling by allowing a larger sample during each respiratory cycle. Monitored expired gases include, for example, physiologic gases and anesthetic gases. If IV anesthesia is also administered, as in "balanced anesthesia," monitoring expired gases will also include measuring concentration in the blood by the breath analysis of the present invention.

In an embodiment, side-stream monitoring is used. Moreover, a water trap, desiccant and/or filter may be used to remove water vapor and condensation from the sample. The device of the present invention continuously samples and measures inspired and exhaled (end-tidal) concentrations of respiratory gases. The monitored gases are both the physiologic gases found in the exhaled breath of patients (oxygen, carbon dioxide, and nitrogen), as well as those administered to the patient by the anesthesiologist in order to induce and maintain analgesia and anesthesia.

The sensors of the present invention may also monitor purity of gases at the entry port (fresh gas entry) and/or carrier gases. If multiple volatile anesthetic agents are connected to the circuit, an appropriate number of sensors may be included to detect each of such agents at the respective entry points as well as prior to inspiration.

Any number of sensors may be used at various points in the circuit to accomplish the desired monitoring. All of the sensors may connect to a single processor for analysis or use multiple processors. Similarly, the results of the monitoring may be displayed through a single display device or multiple display devices as desired. The method and apparatus of the present invention will detect and quantitate the concentration of the target substances.

EXAMPLE 3

Selection of Sensors

The following are examples of various sensor technologies that may be utilized in practicing the method of the present invention:

Microgravimetric Sensors

Microgravimentric sensors are based on the preparation of polymeric- or biomolecule-based sorbents that are selectively predetermined for a particular substance, or group of structural analogs. A direct measurement of mass changes induced by binding of a sorbent with a target marker can be observed by the propagation of acoustic shear waves in the substrate of the sensor. Phase and velocity of the acoustic wave are influenced by the specific adsorption of target markers onto the sensor surface. Piezoelectric materials, such as quartz ($SiO_2$) or zinc oxide (ZnO), resonate mechanically at a specific ultrasonic frequency when excited in an oscillating field. Electromagnetic energy is converted into acoustic energy, whereby piezoelectricity is associated with the electrical polarization of materials with anisotropic crystal structure. Generally, the oscillation method is used to monitor acoustic wave operation. Specifically, the oscillation method measures the series resonant frequency of the resonating sensor. Types of sensors derived from microgravimetric sensors include quartz crystal microbalance (QCM) devices that apply a thickness-shear mode (TSM) and devices that apply surface acoustic wave (SAW) detection principle. Additional devices derived from microgravimetric sensors include the flexural plate wave (FPW), the shear horizontal acoustic plate (SH-APM), the surface transverse wave (STW) and the thin-rod acoustic wave (TRAW).

Conducting Polymers

Conducting polymer sensors promise fast response time, low cost, and good sensitivity and selectivity. The technology is relatively simple in concept. A conductive material, such as carbon, is homogeneously blended in a specific non-conducting polymer and deposited as a thin film on an aluminum oxide substrate. The films lie across two electrical leads, creating a chemoresistor. As the polymer is subjected to various chemical vapors, it expands, increasing the distance between carbon particles, and thereby increasing the resistance. The polymer matrix swells because analyte vapor absorbs into the film to an extent determined by the partition coefficient of the analyte. The partition coefficient defines the equilibrium distribution of an analyte between the vapor phase and the condensed phase at a specified temperature. Each individual detector element requires a minimum absorbed amount of analyte to cause a response noticeable above the baseline noise. Selectivity to different vapors is accomplished by changing the chemical composition of the polymer. This allows each sensor to be tailored to specific chemical vapors. Therefore, for most applications an array of orthogonal responding sensors is required to improve selectivity. Regardless of the number of sensors in the array, the information from them must be processed with pattern recognition software to correctly identify the chemical vapors of interest. Sensitivity concentrations are reportedly good (tens of ppm). The technology is very portable (small and low power consumption), relatively fast in response time (less than 1 minute), low cost, and should be rugged and reliable.

Electrochemical Sensors

Electrochemical sensors measure a change in output voltage of a sensing element caused by chemical interaction of a target marker on the sensing element. Certain electrochemical sensors are based on a transducer principle. For example, certain electrochemical sensors use ion-selective electrodes that include ion-selective membranes, which generate a charge separation between the sample and the sensor surface. Other electrochemical sensors use an electrode by itself as the surface as the complexation agent, where a change in the electrode potential relates to the concentration of the target marker. Further examples of electrochemical sensors are based on semiconductor technology for monitoring charges at the surface of an electrode that has been built up on a metal gate between the so-called source and drain electrodes. The surface potential varies with the target marker concentration.

Additional electrochemical sensor devices include amperometric, conductometric, and capacitive immunosensors. Amperometric immunosensors are designed to measure a current flow generated by an electrochemical reaction at a constant voltage. Generally, electrochemically active labels directly, or as products of an enzymatic reaction, are needed for an electrochemical reaction of a target marker at a sensing electrode. Any number of commonly available electrodes can be used in amperometric immunosensors, including oxygen and $H_2O_2$ electrodes.

Capacitive immunosensors are sensor-based transducers that measure the alteration of the electrical conductivity in a solution at a constant voltage, where alterations in conductivity are caused by biochemical enzymatic reactions, which specifically generate or consume ions. Capacitance changes are measured using an electrochemical system, in which a bioactive element is immobilized onto a pair of metal electrodes, such as gold or platinum electrodes.

Conductometric immunosensors are also sensor-based transducers that measure alteration of surface conductivity. As with capacitive immunosensors, bioactive elements are immobilized on the surface of electrodes. When the bioactive element interacts with a target marker, it causes a decrease in the conductivity between the electrodes.

Electrochemical sensors are excellent for detecting low parts-per-million concentrations. They are also rugged, draw little power, linear and do not require significant support electronics or vapor handling (pumps, valves, etc.) They are moderate in cost ($50 to $200 in low volumes) and small in size.

Gas Chromatography/Mass Spectrometry (GC/MS)

Gas Chromatography/Mass Spectrometry (GC/MS) is actually a combination of two technologies. One technology separates the chemical components (GC) while the other one detects them (MS). Technically, gas chromatography is the physical separation of two or more compounds based on their differential distribution between two phases, the mobile phase and stationary phase. The mobile phase is a carrier gas that moves a vaporized sample through a column coated with a stationary phase where separation takes place. When a separated sample component elutes from the column, a detector converts the column eluent to an electrical signal that is measured and recorded. The signal is recorded as a peak in the chromatogram plot. Chromatograph peaks can be identified from their corresponding retention times. The retention time is measured from the time of sample injection to the time of the peak maximum, and is unaffected by the presence of other sample components. Retention times can range from seconds to hours, depending on the column selected and the component. The height of the peak relates to the concentration of a component in the sample mixture.

After separation, the chemical components need to be detected. Mass spectrometry is one such detection method, which bombards the separated sample component molecules with an electron beam as they elute from the column. This causes the molecules to lose an electron and form ions with a positive charge. Some of the bonds holding the molecule together are broken in the process, and the resulting fragments may rearrange or break up further to form more stable fragments. A given compound will ionize, fragment, and rearrange reproducibly under a given set of conditions. This makes identification of the molecules possible. A mass spectrum is a plot showing the mass/charge ratio versus abundance data for ions from the sample molecule and its fragments. This ratio is normally equal to the mass for that fragment. The largest peak in the spectrum is the base peak. The GC/MS is accurate, selective and sensitive.

Infrared Spectroscopy (FTIR, NDIR)

Infrared (IR) spectroscopy is one of the most common spectroscopic techniques used by organic and inorganic chemists. Simply, it is the absorption measurement of different IR frequencies by a sample positioned in the path of an IR beam. IR radiation spans a wide section of the electromagnetic spectrum having wavelengths from 0.78 to 1000 micrometers (microns). Generally, IR absorption is represented by its wave number, which is the inverse of its wavelength times 10,000. For a given sample to be detected using IR spectroscopy, the sample molecule must be active in the IR region, meaning that the molecule must vibrate when exposed to IR radiation. Several reference books are available which contain this data, including the Handbook of Chemistry and Physics from the CRC Press.

There are two general classes of IR spectrometers—dispersive and non-dispersive. In a typical dispersive IR spectrometer, radiation from a broadband source passes through the sample and is dispersed by a monochromator into component frequencies. The beams then fall on a detector, typically a thermal or photon detector, which generates an electrical signal for analysis. Fourier Transform IR spectrometers (FTIR) have replaced the dispersive IR spectrometer due to their superior speed and sensitivity. FTIR eliminates the physical separation of optical component frequencies by using a moving mirror Michelson interferometer and taking the Fourier transform of the signal.

Conversely, in the non-dispersive IR (NDIR) spectrometer, instead of sourcing a broad IR spectrum for analyzing a range of sample gases, the NDIR sources a specific wavelength which corresponds to the absorption wavelength of the target sample. This is accomplished by utilizing a relatively broad IR source and using spectral filters to restrict the emission to the wavelength of interest. For example, NDIR is frequently used to measure carbon monoxide (CO), which absorbs IR energy at a wavelength of 4.67 microns. By carefully tuning the IR source and detector during design, a high volume production CO sensor is manufactured. This is particularly impressive, as carbon dioxide is a common interferent and has an IR absorption wavelength of 4.26 microns, which is very close to that of CO.

NDIR sensors promise low cost (less than $200), no recurring costs, good sensitivity and selectivity, no calibration and high reliability. They are small, draw little power and respond quickly (less than 1 minute). Warm up time is nominal (less than 5 minutes). Unfortunately, they only detect one target gas. To detect more gases additional spectral filters and detectors are required, as well as additional optics to direct the broadband IR source.

Ion Mobility Spectrometry (IMS)

Ion Mobility Spectrometry (IMS) separates ionized molecular samples on the basis of their transition times when subjected to an electric field in a tube. As the sample is drawn into the instrument, it is ionized by a weak radioactive source. The ionized molecules drift through the cell under the influence of an electric field. An electronic shutter grid allows periodic introduction of the ions into the drift tube where they separate based on charge, mass, and shape. Smaller ions move faster than larger ions through the drift tube and arrive at the detector sooner. The amplified current from the detector is measured as a function of time and a spectrum is generated. A microprocessor evaluates the spectrum for the target compound, and determines the concentration based on the peak height.

IMS is an extremely fast method and allows near real time analysis. It is also very sensitive, and should be able to measure all the analytes of interest. IMS is moderate in cost (several thousand dollars) and larger in size and power consumption.

Metal Oxide Semiconductor (MOS) Sensors

Metal Oxide Semiconductor (MOS) sensors utilize a semiconducting metal-oxide crystal, typically tin-oxide, as the sensing material. The metal-oxide crystal is heated to approximately 400° C., at which point the surface adsorbs oxygen. Donor electrons in the crystal transfer to the adsorbed oxygen, leaving a positive charge in the space charge region. Thus, a surface potential is formed, which increases the sensor's resistance. Exposing the sensor to deoxidizing, or reducing, gases removes the surface potential, which lowers the resistance. The end result is a sensor which changes its electrical resistance with exposure to deoxidizing gases. The change in resistance is approximately logarithmic.

MOS sensors have the advantage of being extremely low cost (less than $8 in low volume) with a fast analysis time (milliseconds to seconds). They have long operating lifetimes (greater than five years) with no reported shelf life issues.

Thickness-Shear Mode Sensors (TSM)

TSM sensors consist of an AT-cut piezoelectric crystal disc, most commonly of quartz because of its chemical stability in biological fluids and resistance to extreme temperatures, and two electrodes (preferably metal) attached to opposite sides of the disc. The electrodes apply the oscillating electric field. Generally, TSM sensor devices are run in a range of 5-20 MHz. Advantages are, besides the chemical inertness, the low cost of the devices and the reliable quality of the mass-produced quartz discs.

Photo-Ionization Detectors (PID)

Photo-Ionization Detectors rely on the fact that all elements and chemicals can be ionized. The energy required to displace an electron and 'ionize' a gas is called its Ionization Potential (IP), measured in electron volts (eV). A PID uses an ultraviolet (UV) light source to ionize the gas. The energy of the UV light source must be at least as great as the IP of the sample gas. For example, benzene has an IP of 9.24 eV, while carbon monoxide has an IP of 14.01 eV. For the PID to detect the benzene, the UV lamp must have at least 9.24 eV of energy. If the lamp has an energy of 15 eV, both the benzene and the carbon monoxide would be ionized. Once ionized, the detector measures the charge and converts the signal information into a displayed concentration. Unfortunately, the display does not differentiate between the two gases, and simply reads the total concentration of both summed together.

Three UV lamp energies are commonly available: 9.8, 10.6 and 11.7 eV. Some selectivity can be achieved by selecting the lowest energy lamp while still having enough energy to ionize the gases of interest. The largest group of compounds measured by a PID are the organics (compounds containing carbon), and they can typically be measured to parts per million (ppm) concentrations. PIDs do not measure any gases with an IP greater than 11.7 eV, such as nitrogen, oxygen, carbon dioxide and water vapor. The CRC Press Handbook of Chemistry and Physics includes a table listing the IPs for various gases.

PIDs are sensitive (low ppm), low cost, fast responding, portable detectors. They also consume little power.

Surface Acoustic Wave Sensors (SAW)

Surface Acoustic Wave (SAW) sensors are constructed with interdigitated metal electrodes fabricated on piezoelectric substrates both to generate and to detect surface acoustic waves. Surface acoustic waves are waves that have their maximum amplitude at the surface and whose energy is nearly all contained within 15 to 20 wavelengths of the surface. Because the amplitude is a maximum at the surface such devices are very surface sensitive. Normally, SAW devices are used as electronic bandpass filters in cell phones. They are hermetically packaged to insure that their performance will not change due to a substance contacting the surface of the SAW.

SAW chemical sensors take advantage of this surface sensitivity to function as sensors. To increase specificity for specific compounds, SAW devices are frequently coated with a thin polymer film that will affect the frequency and insertion loss of the device in a predictable and reproducible manner. Each sensor in a sensor array is coated with a different polymer and the number and type of polymer coating are selected based on the chemical to be detected. If the device with the polymer coating is then subjected to chemical vapors that absorb into the polymer material, then the frequency and insertion loss of the device will further change. It is this final change that allows the device to function as a chemical sensor.

If several SAW devices are each coated with a different polymer material, the response to a given chemical vapor will vary from device to device. The polymer films are normally chosen so that each will have a different chemical affinity for a variety of organic chemical classes, that is, hydrocarbon, alcohol, ketone, oxygenated, chlorinated, and nitrogenated. If the polymer films are properly chosen, each chemical vapor of interest will have a unique overall effect on the set of devices. SAW chemical sensors are useful in the range of organic compounds from hexane on the light, volatility extreme to semi-volatile compounds on the heavy, low volatility extreme.

Motors, pumps and valves are used to bring the sample into and through the array. The sensitivity of the system can be enhanced for low vapor concentrations by having the option of using a chemical preconcentrator before the array. In operation, the preconcentrator absorbs the test vapors for a period of time and is then heated to release the vapors over a much shorter time span thereby increasing the effective concentration of the vapor at the array. The system uses some type of drive and detection electronics for the array. An on board microprocessor is used to control the sequences of the system and provide the computational power to interpret and analyze data from the array.

SAW sensors are reasonably priced (less than $200) and have good sensitivity (tens of ppm) with very good selectivity. They are portable, robust and consume nominal power. They warm up in less than two minutes and require less than one minute for most analysis. They are typically not used in high accuracy quantitative applications, and thus require no calibration. SAW sensors do not drift over time, have a long operating life (greater than five years) and have no known shelf life issues. They are sensitive to moisture, but this is addressed with the use of a thermally desorbed concentrator and processing algorithms.

Amplifying Fluorescent Polymer Technology

Sensors can use fluorescent polymers that react with volatile chemicals as sensitive target marker detectors. Conventional fluorescence detection normally measures an increase or decrease in fluorescence intensity or an emission wavelength shift that occurs when a single molecule of the target marker interacts with an isolated chromophore, where the chromophore that interacts with the target marker is quenched; the remaining chromophores continue to fluoresce.

A variation of this approach is the "molecular wire" configuration, as described by Yang and Swager, *J. Am. Chem. Soc.*, 120:5321-5322 (1998) and Cumming et al., *IEEE Trans Geoscience and Remote Sensing*, 39:1119-1128 (2001), both of which are incorporated herein by reference in their entirety. In the molecular wire configuration, the absorption of a single photon of light by any chromophore will result in a chain reaction, quenching the fluorescence of many chromophores and amplifying the sensory response by several orders of magnitude. Sensors based on the molecular wire configuration have been assembled for detecting explosives (see Swager and Wosnick, *MRS Bull*, 27:446-450 (2002), which is incorporated herein by reference in its entirety.

Fiber Optic Microsphere Technology

Fiber optic microsphere technology is based upon an array of a plurality of microsphere sensors (beads), wherein each microsphere belongs to a discrete class that is associated with a target marker, that is placed on an optical substrate containing a plurality of micrometer-scale wells (see, for example, Michael et al., *Anal Chem*, 71:2192-2198 (1998); Dickinson et al., *Anal Chem.*, 71:2192-2198 (1999); Albert and Walt, *Anal Chem*, 72:1947-1955 (2000); and Stitzel et al., *Anal Chem*, 73:5266-5271 (1001), all of which are incorporated herein by reference in their entirety). Each type of bead is encoded with a unique signature to identify the bead as well as its location. Upon exposure to a target marker, the beads respond to the target marker and their intensity and wavelength shifts are used to generate fluorescence response patterns, which are, in turn, compared to known patterns to identify the target marker.

Interdigitated Microelectrode Arrays (IME)

Interdigitated microelectrode arrays are based on the used of a transducer film that incorporates an ensemble of nanometer-sized metal particles, each coated by an organic monomolecular layer shell (see, for example, Wohltjen and Snow, *Anal Chem*, 70:2856-2859 (1998); and Jarvis et al., *Proceedings of the 3$^{rd}$ Intl Aviation Security Tech Symposium*, Atlantic City, N.J., 639-647 (2001), both of which are incorporated hereinbyreference in their entirety). Such sensor devices are also known as metal-insulator-metal ensembles (MIME) because of the combination of a large group of colloidal-sized, conducting metal cores separated by thin insulating layers.

Microelectromechanical Systems (MEMS)

Sensor technology based on MEMS integrate mechanical elements, sensors, actuators, and electronics on a common silicon substrate for use in detecting target markers (see, for example, Pinnaduwage et al., *Proceedings of 3$^{rd}$ Intl Aviation Security Tech Symposium*, Atlantic City, N.J., 602-615 (2001); and Lareau et al., *Proceedings of 3$^{rd}$ Intl Aviation Security Tech Symposium*, Atlantic City, N.J., 332-339 (2001), both of which are incorporated herein by reference in their entirety).

One example of sensor technology based on MEMS is microcantilever sensors. Microcantilever sensors are hairlike, silicon-based devices that are at least 1,000 times more sensitive and smaller than currently used sensors. The working principle for most microcantilever sensors is based on a measurement of displacement. Specifically, in biosensor applications, the displacement of a cantilever-probe is related to the binding of molecules on the (activated) surface of the cantilever beam, and is used to compute the strength of these bonds, as well as the presence of specific reagents in the solution under consideration (Fritz, J. et al., "Translating biomolecular recognition into nanomechanics," *Science*, 288: 316-318 (2000); Raiteri, R. et al., "Sensing of biological substances based on the bending of microfabricated cantilevers," *Sensors and Actuators B*, 61:213-217 (1999), both of which are incorporated herein by reference in their entirety). It is clear that the sensitivity of these devices strongly depends on the smallest detectable motion, which poses a constraint on the practically vs. theoretically achievable performance.

One example of microcantilever technology uses silicon cantilever beams (preferably a few hundred micrometers long and 1 μm thick) that are coated with a different sensor/detector layer (such as antibodies or aptamers). When exposed to a target marker, the cantilever surface absorbs the target marker, which leads to interfacial stress between the sensor and the absorbing layer that bends the cantilever. Each cantilever bends in a characteristic way typical for each target marker. From the magnitude of the cantilever's bending response as a function of time, a fingerprint pattern for each target marker can be obtained.

Microcantilever sensors are highly advantageous in that they can detect and measure relative humidity, temperature, pressure, flow, viscosity, sound, ultraviolet and infrared radiation, chemicals, and biomolecules such as DNA, proteins, and enzymes. Microcantilever sensors are rugged, reusable, and extremely sensitive, yet they cost little and consume little power. Another advantage in using the sensors is that they work in air, vacuum, or under liquid environments.

Molecularly Imprinted Polymeric Film

Molecular imprinting is a process of template-induced formation of specific molecular recognition sites (binding or catalytic) in a polymeric material where the template directs the positioning and orientation of the polymeric material's structural components by a self-assembling mechanism (see, for example, Olivier et al., *Anal Bioanal Chem*, 382:947-956 (2005); and Ersoz et al., *Biosensors & Bioelectronics*, 20:2197-2202 (2005), both of which are incorporated herein by reference in their entirety). The polymeric material can include organic polymers as well as inorganic silica gels. Molecularly imprinted polymers (MIPs) can be used in a variety of sensor platforms including, but not limited to, fluorescence spectroscopy; UVN is spectroscopy; infrared spectroscopy; surface plasmon resonance; chemiluminescent adsorbent assay; and reflectometric interference spectroscopy. Such approaches allow for the realization of highly efficient and sensitive target marker recognition.

EXAMPLE 4

Detection of Glucose in Exhaled Breath

Persons with diabetes presently check their blood glucose levels between 1 and 6-8 times each day. Knowledge of blood glucose levels is an absolute necessity for guiding proper administration and dosing of insulin and other medications used to control hyperglycemia. Presently the person must draw blood samples, usually from a finger using a lancet device, and place the sample on a "test strip" which is inserted into a glucose monitor that gives the blood glucose concentration. This process requires considerable skill, time and subjects the person with diabetes to immediate recognition as a diabetic and thus results in the potential for embarrassment and even prejudice and/or discrimination when applying for employment.

An attractive alternative is to use a sensor system that collects a sample of exhaled breath which for compounds such as glucose, which are extremely hydrophilic, condenses the sample into a "condensate" which is then placed in contact with the sensor by a pump or microfluidic system. Thus, persons with diabetes are far more likely to inconspicuously blow into a small hand-held device that provides a blood glucose concentration from an exhaled breath sample then to perform the multiple steps required for a blood sample, particularly in public places. This technology is likely to increase the acceptance of frequent blood glucose monitoring and reduce the embarrassment that many persons with diabetes feel when having to draw blood samples from their fingers.

EXAMPLE 5

Measurement of Blood Glucose and Lacetic Acid Concentrations in the Operating Room During Surgical Procedures Using Exhaled Breath An elderly patient with a history of insulin dependent diabetes (Type I) requires a serious operation in which significant blood loss is anticipated. As part of the routine monitoring of the patient, the anesthesiologist continuously monitors exhaled breath glucose and lacetic acid. Several recent medical research studies have shown that tight control of glucose in the normal range improves outcome, wound healing and rate of post-operative infection in persons with diabetes. Presently, the anesthesiologist can only monitor blood glucose intermittently by drawing blood samples. These results guide the administration of insulin. Excessive doses can lead to hypoglycemia, with disastrous consequences and inadequate doses can lead to hyperglycemia, which can result in intra- and post-operative complications. Exhaled breath affords the potential of continuous tight glucose control without the potential for either hyperglycemia or hypoglycemia. In fact, a "closed loop" system is possible where the exhaled breath glucose concentration is used to control and insulin infusion, thus freeing the anesthesiologist of having to give boluses of insulin.

In addition to monitoring glucose continuously, the anesthesiologist monitors exhaled breath lacetic acid to determine whether there is excessive blood loss or other reasons for decrease perfusion of vital organs. Presently, blood pressure, heart rate and on occasions, central venous pressure are used to monitor patients for blood loss with resulting hypovolemia and diminished perfusion. This in turn leads to lacetic acidosis, an ominous complication, but presently lacetic acid can only be measured intermittently from blood samples. By continuously monitoring lacetic acid levels in exhaled breath condensate, the anesthesiologist will have a much better means of determining if there is hypoperfusion of vital organs. Thus, measurement of compounds continuously in exhaled breath in either the gaseous or condensed state can lead to marked improvement in monitoring, and therefore, treatment of patients in the operating room and the intensive care unit.

It should be understood that the examples and embodiments described herein are for illustrative purposes only and that various modifications or changes in light thereof will be suggested to persons skilled in the art and are to be included within the spirit and purview of this application and the scope of the appended claims. Specifically, the marker detection method of the present invention is intended to cover detection not only through the exhalation by a patient with a device utilizing electronic nose technology, but also other suitable technologies, such as gas chromatography, transcutaneous/transdermal detection, semiconductive gas sensors, mass spectrometers, IR or UV or visible or fluorescence spectrophotometers.

All patents, patent applications, provisional applications, and publications referred to or cited herein, or from which a claim for benefit of priority has been made, are incorporated by reference in their entirety to the extent they are not inconsistent with the explicit teachings of this specification.

We claim:

1. An anesthetic agent delivery system or apparatus for intravenously delivering a desired dose of anesthetic agent to a patient comprising:
   (a) an intravenous anesthetic supply;
   (b) a breath analyzer for analyzing the patient's breath for concentration of at least one substance, selected from the group consisting of the active anesthetic agent itself or a metabolite thereof, indicative of the anesthetic agent concentration in the patient's bloodstream, and for providing a signal to indicate the anesthetic agent concentration delivered to the patient; and
   (c) a system controller connected to the anesthetic supply which receives the signal and controls the amount of anesthetic agent based on the signal.

2. The system or apparatus of claim 1 wherein the breath analyzer comprises a collector for sampling the patient's expired breath, a sensor for analyzing the breath for concentration of at least one substance indicative of the anesthetic agent concentration, a processor for calculating the effect of the agent based on the concentration and determining depth of anesthesia.

3. The system or apparatus of claim 2 wherein the sensor is selected from semiconductor gas sensor technology, surface acoustic wave gas sensor technology or conductive polymer gas sensor technology.

4. The system or apparatus of claim 1, further comprising respiratory phase sensor technology for determining a specific phase of the respiratory cycle from which the sample of breath is collected.

5. The system or apparatus of claim 4, wherein said respiratory phase sensor technology is selected from the group consisting of:
   viscosity sensors; flow sensors; pressure sensors; humidity sensors;
   temperature sensors; and gas sensors.

6. The system or apparatus of claim 5, wherein said respiratory phase sensor technology is selected from the group consisting of:
   $CO_2$ sensors; $O_2$ sensors; and NO sensors.

7. The system or apparatus of claim 4, wherein the sample of breath is collected from the initial phase or end-tidal phase.

8. The system or apparatus according to claim 1 wherein said anesthetic agent supply comprises an anesthetic gas supply in addition to said intravenous agent supply.

9. The system or apparatus according to claim 8 comprising both an anesthetic gas supply and an intravenous agent supply, and wherein said controller controls the amount of anesthetic gas supply to a breathing circuit including said patient, said controller controls the amount of intravenous agent administered to the patient intravenously, or both, or wherein separate controllers control the amount of said anesthetic gas supply to a breathing circuit including said patient and the amount of intravenous agent administered to the patient intravenously.

10. The system or apparatus according to claim 8 further comprising an inspired gas analyzer for analyzing the concentration of anesthetic gas in the breathing circuit.

11. The system or apparatus according to claim 10 wherein said controller is connected to both an intravenous anesthetic supply and an anesthetic gas supply and which receives signals from both an inspired gas analyzer and an expired gas analyzer and controls the amount of anesthetic agents administered based on the signals or wherein a first controller receives a signal from an inspired gas analyzer and a second controller receives a signal from an expired gas analyzer, and each of said first and second controllers control the amount of anesthetic agent delivered to a patient based on said signals.

12. The system or apparatus of claim 11 wherein the inspired gas analyzer and expired gas analyzer each comprise a sensor for analyzing the gas for concentration of at least one substance indicative of anesthetic agent concentration and a processor for calculating the effect of the agent based on the concentration and determining depth of anesthesia.

13. The system or apparatus of claim 12 wherein the sensor is selected from semiconductor gas sensor technology, surface acoustic wave gas sensor technology or conductive polymer gas sensor technology and further, optionally comprising: respiratory phase sensor technology for determining a specific phase of the respiratory cycle from which the sample of breath is collected, and the sample of breath is collected from the initial phase or end-tidal phase.

14. The system or apparatus according to claim 1 for intravenously delivering a desired dose of anesthetic agent to a patient comprising:
   an intravenous anesthetic supply having a controller for controlling the amount of anesthetic agent provided intravenously by the supply;
   a breath analyzer for analyzing the patient's breath for concentration of at least one substance indicative of the free anesthetic agent concentration in the patient's bloodstream that provides a signal to indicate the free anesthetic agent concentration produced by the anesthetic agent intravenously delivered to the patient; and
   a system controller connected to the anesthetic supply which receives the signal and controls the amount of anesthetic agent delivered intravenously based on the signal.

15. The system or apparatus of claim 14 wherein the breath analyzer comprises a collector for sampling the patient's expired breath, a sensor for analyzing the breath for concentration of at least one substance indicative of the free anesthetic agent concentration in the patient's blood, a processor for calculating the effect of the agent based on the concentration and determining depth of anesthesia.

16. The system or apparatus of claim 15 wherein the sensor is selected from semiconductor gas sensor technology, conductive polymer gas sensor technology, or surface acoustic wave gas sensor technology.

17. The system or apparatus according to claim 14 wherein said anesthetic agent is selected from the group comprising Remifentanil and Propofol.

18. The system or apparatus of claim 14 wherein the breath analyzer comprises a collector for sampling the patient's expired breath, and a sensor for analyzing the breath for concentration of at least one substance indicative of the free anesthetic agent concentration in the patient's blood.

19. The system or apparatus according to claim 1 for measuring the free concentration in blood of a patient of an intravenously administered anesthetic comprising:
   a breath analyzer for analyzing the patient's breath for concentration of at least one substance indicative of the anesthetic agent in the patient's bloodstream.

20. The system or apparatus according to claim 19 wherein said anesthetic is selected from the group comprising Remifentanil and Propofol.

21. The apparatus according to claim 19 further comprising a means for determining the fraction of the breath collected for analysis such that any particular breath fraction may be collected, including the only the end tidal breath fraction.

22. An anesthetic agent delivery system or apparatus for delivering a desired dose of anesthetic agent to a patient comprising:
   (a) an anesthetic supply;
   (b) a breath analyzer for analyzing the patient's breath for concentration of at least one substance indicative of the anesthetic agent concentration in the patient's bloodstream, and for providing a signal to indicate the anesthetic agent concentration delivered to the patient; and
   (c) a system controller connected to the anesthetic supply which receives the signal and controls the amount of anesthetic agent based on the signal;
   wherein the breath analyzer comprises a collector for sampling the patient's expired breath, a sensor for analyzing the breath for concentration of at least one substance indicative of the anesthetic agent concentration, a processor for calculating the effect of the agent based on the concentration and determining depth of anesthesia.

23. The system or apparatus of claim 22 wherein the sensor is selected from semiconductor gas sensor technology, surface acoustic wave gas sensor technology or conductive polymer gas sensor technology.

24. An anesthetic agent delivery system or apparatus for delivering a desired dose of anesthetic agent to a patient comprising:
   (a) an anesthetic supply;
   (b) a breath analyzer for analyzing the patient's breath for concentration of at least one substance indicative of the anesthetic agent concentration in the patient's bloodstream, and for providing a signal to indicate the anesthetic agent concentration delivered to the patient; and
   (c) a system controller connected to the anesthetic supply which receives the signal and controls the amount of anesthetic agent based on the signal;
   wherein said anesthetic agent supply comprises an anesthetic gas supply, an intravenous agent supply;
   further comprising an inspired gas analyzer for analyzing the concentration of anesthetic gas in the breathing circuit;
   wherein said controller is connected to both an intravenous anesthetic supply and an anesthetic gas supply and which receives signals from both an inspired gas analyzer and an expired gas analyzer and controls the amount of anesthetic agents administered based on the signals or wherein a first controller receives a signal from an inspired gas analyzer and a second controller receives a signal from an expired gas analyzer, and each of said first and second controllers control the amount of anesthetic agent delivered to a patient based on said signals;
   wherein the inspired gas analyzer and expired gas analyzer each comprise a sensor for analyzing the gas for concentration of at least one substance indicative of anesthetic agent concentration and a processor for calculating the effect of the agent based on the concentration and determining depth of anesthesia.

25. The system or apparatus of claim 24 wherein the sensor is selected from semiconductor gas sensor technology, surface acoustic wave gas sensor technology or conductive polymer gas sensor technology and further, optionally comprising: respiratory phase sensor technology for determining a specific phase of the respiratory cycle from which the sample of breath is collected, and the sample of breath is collected from the initial phase or end-tidal phase.

26. An anesthetic agent delivery system or apparatus for delivering a desired dose of anesthetic agent to a patient comprising:
   (a) an anesthetic supply;
   (b) a breath analyzer for analyzing the patient's breath for concentration of at least one substance indicative of the anesthetic agent concentration in the patient's bloodstream, and for providing a signal to indicate the anesthetic agent concentration delivered to the patient; and
   (c) a system controller connected to the anesthetic supply which receives the signal and controls the amount of anesthetic agent based on the signal;
   said system for intravenously delivering a desired dose of anesthetic agent to a patient comprising:
   an intravenous anesthetic supply having a controller for controlling the amount of anesthetic agent provided intravenously by the supply;
   a breath analyzer for analyzing the patient's breath for concentration of at least one substance indicative of the free anesthetic agent concentration in the patient's bloodstream that provides a signal to indicate the free anesthetic agent concentration produced by the anesthetic agent intravenously delivered to the patient; and
   a system controller connected to the anesthetic supply which receives the signal and controls the amount of anesthetic agent delivered intravenously based on the signal;
   wherein the breath analyzer comprises a collector for sampling the patient's expired breath, a sensor for analyzing the breath for concentration of at least one substance indicative of the free anesthetic agent concentration in the patient's blood, a processor for calculating the effect of the agent based on the concentration and determining depth of anesthesia.

27. The system or apparatus of claim 25 wherein the sensor is selected from semiconductor gas sensor technology, conductive polymer gas sensor technology, or surface acoustic wave gas sensor technology.

* * * * *